United States Patent [19]
Pausch et al.

[11] Patent Number: 5,691,188
[45] Date of Patent: Nov. 25, 1997

[54] TRANSFORMED YEAST CELLS EXPRESSING HETEROLOGOUS G-PROTEIN COUPLED RECEPTOR

[75] Inventors: Mark Henry Pausch, Robbinsville, N.J.; Bradley A. Ozenberger, Yardley, Pa.; John Richard Hadcock, Mount Holly, N.J.; Laura Alicia Price, Langhorne, Pa.; Eileen Marie Kajkowski, Ringoes, N.J.; Donald Richard Kirsch, Princeton, N.J.; Deborah Tardy Chaleff, Pennington, N.J.

[73] Assignee: American Cyanamid Company, Madison, N.J.

[21] Appl. No.: 195,729

[22] Filed: Feb. 14, 1994

[51] Int. Cl.$^6$ .................................................. C12N 15/81
[52] U.S. Cl. ............... 435/254.2; 435/69.1; 435/254.21; 435/320.1; 536/23.1
[58] Field of Search .......................... 435/255.1, 320.1, 435/69.1, 254.21, 254.2; 536/23.1

[56] References Cited

U.S. PATENT DOCUMENTS 5,284,746  2/1994  Sledziewski .................... 435/6

FOREIGN PATENT DOCUMENTS

WO 92/05244  9/1991  WIPO.

OTHER PUBLICATIONS

Dohlman, et al., Model Systems for the Study of Seven-Transmembrane-segment Receptors, vol. 60, pp. 653–688, Annu. Rev. Biochem, 1991.

Sprague et al., The Molecular Cellular Biology of the Yeast *Sacchromyces cerevisiae;* Gene Expression, vol. II, pp. 657–643 1992, Cold Spring Harbor.

*Primary Examiner*—Stephen G. Walsh
*Assistant Examiner*—Sally Teng

[57] ABSTRACT

A first aspect of the present invention is directed to a transformed yeast cell containing a first heterologous DNA sequence which codes for a G protein-coupled receptor, for example, the somatostatin receptor, and a second heterologous DNA sequence which codes for a G protein α subunit or portions thereof fused to DNA sequences from the yeast G protein a subunit. A second aspect of the present invention is a transformed yeast cell containing a heterologous DNA sequence which codes for a G protein coupled receptor. A third aspect of the present invention is a method of assaying compounds to determine effects on cell growth.

31 Claims, 17 Drawing Sheets

| | | Bmax (pmol/mg) |
|---|---|---|
| CHI11 |  | 3.1 |
| CHI17 | 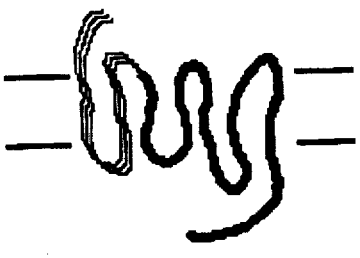 | 1.6 |
| CHI18 |  | 0.7 |
FIG. 4

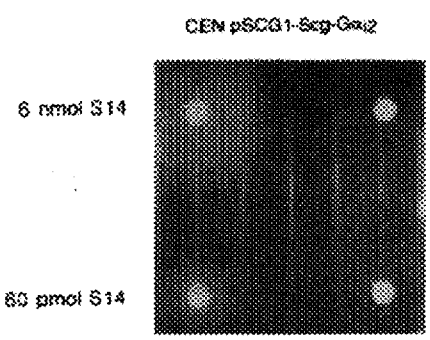
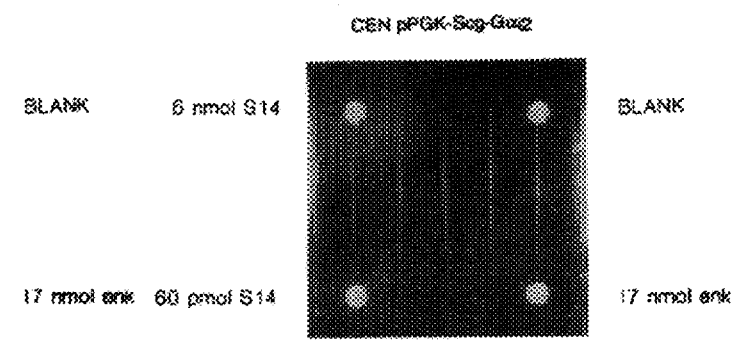
FIG. 14A
FIG. 14B
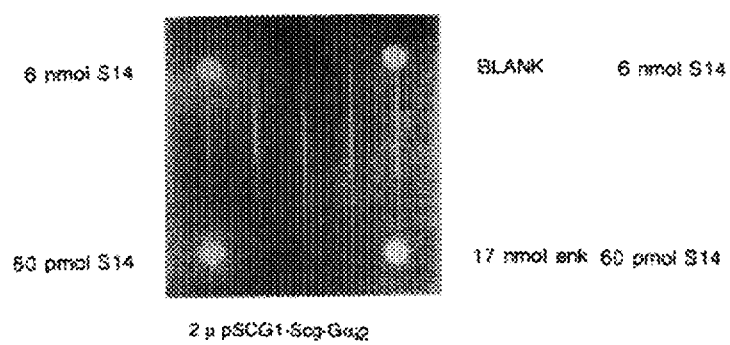
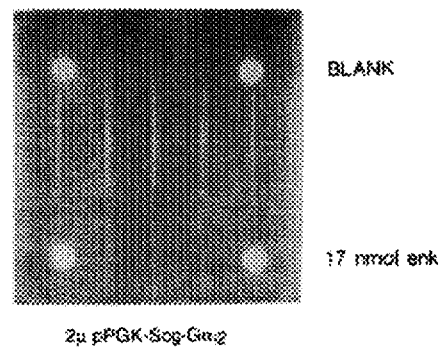
FIG. 14C
FIG. 14D

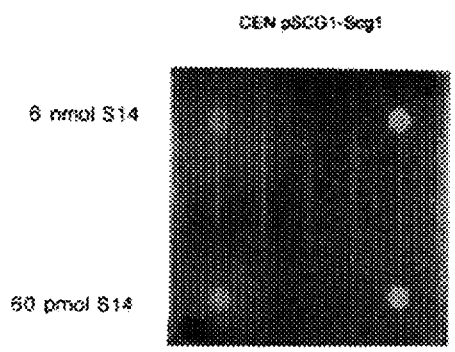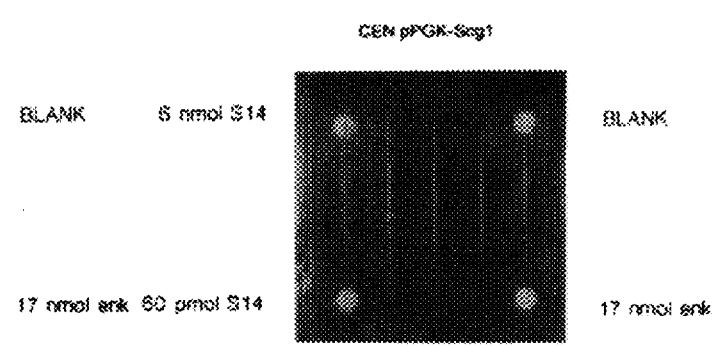
FIG. 15A   FIG. 15B
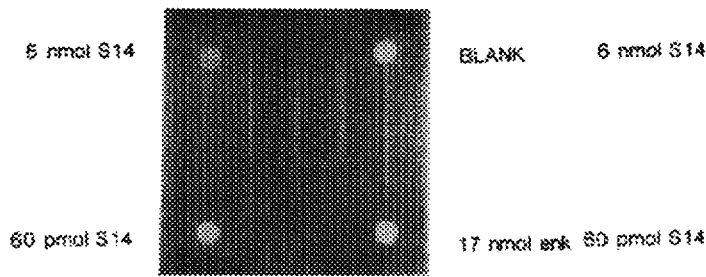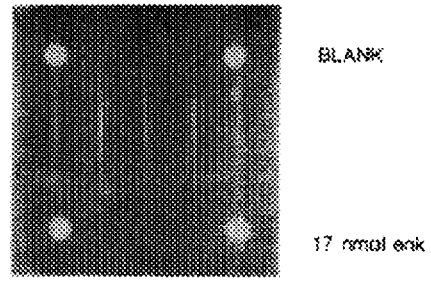
FIG. 15C   FIG. 15D

TRANSFORMED YEAST CELLS EXPRESSING HETEROLOGOUS G-PROTEIN COUPLED RECEPTOR

FIELD OF INVENTION

This invention relates to yeast cells expressing heterologous G protein-coupled receptors, vectors useful for making such cells, and methods of using the same.

BACKGROUND OF THE INVENTION

The actions of many extracellular signals, for example: neurotransmitters, hormones, odorants and light, are mediated by receptors with seven transmembrane domains (G protein-coupled receptors) and heterotrimeric guanine nucleotide-binding regulatory proteins (G proteins). For a review, see H. G. Dohlman, J. Thorner, M. Caron, and R. J. Lefkowitz, Ann. Rev. Biochem, 60, 653–688 (1991). G protein-mediated signaling systems are present in organisms as divergent as yeast and man. The yeast *Saccharomyces cerevisiae* is utilized as a model eukaryotic organism. Due to the ease with which one can manipulate the genetic constitution of the yeast *Saccharomyces cerevisiae*, researchers have developed a detailed understanding of many complex biological pathways. It has been demonstrated in numerous systems that the evolutionary conservation of protein structure is such that many heterologous proteins can substitute for their yeast equivalents. For example, mammalian Gα proteins can form heterotrimeric complexes with yeast Gβγ proteins [Kang, Y. -S., Kane, J., Kurjan, J., Stadel, J. M., and Tipper, D. J. (1990) Mol. Cell. Biol. 10, 2582–2590]. The G protein-coupled receptors represent important targets for new therapeutic drugs. Discovery of such compounds will necessarily require screening assays of high specificity and throughput. For example, therapeutic intervention in the somatostatin-growth hormone axis requires new chemical agents that act in a somatostatin receptor subtype-selective manner. Screening assays utilizing yeast strains genetically modified to accommodate functional expression of the G protein-coupled receptors offer significant advantages in this area.

G protein-coupled pheromone receptors in yeast control a developmental program that culminates in mating (fusion) of a and a haploid cell types to form the a/α diploid (for a review, see G. F. Sprague, Jr. and J. W. Thorner, in The Molecular Biology and Cellular Biology of the Yeast Saccharomyces: volume II, Gene Expression). The process of mating is initiated by extracellular peptides, the mating pheromones. Cells of the a mating type secrete α-factor, which elicits a response in α-cells; cells of the α-mating type secrete α-factor which acts only on a cells. Haploid cells respond to the presence of the peptide mating pheromones through the action of endogenous G protein-coupled pheromone receptors (STE2: the α-factor receptor, expressed only in α cells and STE3: the α-factor receptor expressed only in α-cells). Both receptors interact with the same tripartite G proteins and a signal transduction cascade that is common to both haploid cell types. Upon pheromone-binding to receptor, the receptor presumably undergoes a conformational change leading to activation of the G protein. The α-subunit, SCG1/GPA1, exerts a negative effect on the pheromone response pathway, which is relieved by receptor-dependent activation. The complex of βγ subunits (STE4, STE18) is thought to transmit the positive signal to an effector, possibly STE20, a putative protein kinase [Leberer, E., Dignard, D., Harcus, D., Thomas, D. Y., Whiteway, M. (1992) EMBO J. 11, 4815–4824]. The effector in turn activates downstream elements of the signal transduction pathway which include STE5, and a presumptive protein kinase cascade composed of the products of the STE11, STE7, FUS3 and KSS1 genes, eventually resulting in cell cycle arrest and transcription induction. The primary interface between elements of the pheromone response pathway and cell cycle regulatory machinery is the FAR1 gene product. Certain recessive alleles of FAR1 and FUS3 fail to undergo cell cycle arrest in response to pheromone, while permitting pheromone dependent transcription to occur. Pheromone-dependent transcription is mediated through the action of the sequence-specific DNA-binding protein STE12. Activation of STE12 results in transcription of genes possessing a cis-acting DNA sequence, the pheromone response element. These pheromone responsive genes encode products that are required for pheromone synthesis (MFa1, MFa2, MFA1, MFA2, STE6, STE13) and the response to pheromone (STE2, STE3, SCG1/GPA1, FUS3), facilitate or participate in cell association and fusion (FUS1), cell cycle arrest (FAR1), and the morphological events required for mating. In the event that the mating process is not consummated, yeast cells become adapted to the presence of pheromone and resume mitotic growth. The mating signal transduction pathway is known to become desensitized by several mechanisms including pheromone degradation and modification of the function of the receptor, G proteins and/or downstream elements of the pheromone signal transduction by the products of the SST2, STE50, AFR1 [Konopka, J. B. (1993) Mol. Cell. Biol. 13, 6876–6888], and SGV1 genes. Selected mutations in these genes can lead to hypersensitivity to pheromone and an inability to adapt to the presence of pheromone. Introduction of a constellation of mutations in the mating signal transduction pathway results in a yeast cell well suited to expression of heterologous G protein-coupled receptors and able to functionally respond to their cognate ligands.

The somatostatin receptor (SSTR) is a prototype of the seven-transmembrane-domain class of receptors in mammalian cells. The cyclic tetradecapeptide somatostatin, first isolated from hypothalamus and shown to be a potent inhibitor of growth hormone release from the anterior pituitary, has been shown to have broad modulatory effects in CNS and peripheral tissues. In response to binding of somatostatin, SSTR activates a heterotrimic G protein, which in turn modifies the activity of a variety of effector proteins including but not limited to adenylate cyclases, ion channels, and phospholipases. The effects of somatostatin are transduced through the action of gene products encoded in five distinct receptor subtypes that have recently been cloned [Strnad, J., Eppler, C. M., Corbett, M., and Hadcock, J. R. (1993) BBRC 191, 968–976; Yamada, Y., Post, S. R., Wang, K., Tager, H. S., Bell, G. I., and Seino, S. (1992) Proc. Natl. Acad. Sci. U.S.A 89, 251–255; Meyerhof, W., Paust, H. -J., Schonrock, C., and Richter, D. (1991); Kluxen, F. -W., Bruns, C., and Lubbert, H. (1992) Proc. Natl. Acad. Sci. U.S.A 89, 4618–4622; Li, X. -J., Forte, M., North, R. A., Ross, C. A., and Snyder, S. (1992) J. Biol. Chem. 267, 21307–21312; Bruno, J. F., Xu, Y., Song, J., and Berelowitz, M. (1992) Proc. Natl. Acad. Sci. U.S.A 89, 11151–11154; O'Carrol, A. -M., Lolait, S. J., Konig, M., and Mahan, L. (1992) Mol. Pharmocol. 42, 939–946].

G proteins are comprised of three subunits: a guanyl-nucleotide binding α subunit; a β subunit; and a γ submit [for a review, see Conklin, B. R and Bourne, H. R. (1993) Cell 73, 631–641]. G proteins cycle between two forms, depending on whether GDP or GTP is bound to the α subunit thereto. When GDP is bound, the G protein exists as an heterotrimer, the Gαβγ complex. When GTP is bound, the a subunit dissociates, leaving a Gβγ complex. Importantly, when a Gαβγ complex operatively associates with an activated G protein coupled receptor in a cell membrane, the rate of exchange of GTP for bound GDP is increased and, hence, the rate of dissociation of the bound Gα subunit from the Gβγ complex increases. The free Gα subunit and Gβγ complex are capable of transmitting a signal to downstream elements of a variety of signal transduction pathways. This fundamental scheme of events forms the basis for a multiplicity of different cell signaling phenomena.

SUMMARY OF THE INVENTION

A first aspect of the present invention is directed to a transformed yeast cell containing a first heterologous DNA sequence which codes for a G protein-coupled receptor, for example, the somatostatin receptor, and a second heterologous DNA sequence which codes for a G protein α subunit or portions thereof fused to DNA sequences from the yeast G protein a subunit. The cell contains a third heterologous DNA sequence comprising a pheromone-responsive promoter and an indicator gene positioned downstream from the pheromone-responsive promoter and operatively associated therewith. The cell further contains several mutations. These include 1) a mutation of the SCG1/GPA1 gene, which inactivates the yeast Gα protein, facilitating interaction of the heterologous receptor with the heterologous G protein; 2) a mutation of the FAR1 gene, which inactivates its function and enables the yeast cell to continue growing in spite of activation of the pheromone response signal transduction pathway; and, 3) a mutation of the SST2 gene, the effect of the which is to greatly increase the sensitivity of the response of the cell to receptor-dependent activation of the pheromone response signal transduction pathway.

A second aspect of the present invention is a transformed yeast cell containing a heterologous DNA sequence which codes for a G protein coupled receptor. The cell contains a second heterologous DNA sequence comprising a pheromone-responsive promotor and an indicator gene positioned downstream from the pheromone-responsive promoter and operatively associated therewith. The cell further contains several mutations. These include 1) a mutation of the FAR1 gene, which inactivates its function and enables the yeast cell to continue growing in spite of activation of the pheromone response signal transduction pathway; and, 2) a mutation of the SST2 gene, the effect of which is to greatly increase the sensitivity of the response of the cell to receptor-dependent activation of the pheromone response signal transduction pathway. A productive signal is detected in a bioassay through coupling of the heterologous receptor to the yeast Gα protein.

A third aspect of the present invention is a method of assaying compounds to determine effects on cell growth. Yeast cells of the kind described above are cultured in appropriate growth medium to cause expression of heterologous proteins, embedded in agar growth medium, and exposed to chemical compounds applied to the surface of the agar plates. Effects on the growth of embedded cells are expected around compounds that activate the heterologous receptor.

BRIEF DESCRIPTION OF THE DRAWINGS

FIG. 4. Amino-terminal chimeric Ste2/5HT1a receptors. The CHI11 receptor contains the first 14 amino acids of the yeast Ste2 protein. The CHI17 receptor has a replacement of the amino-terminus of the 5HT1a receptor through the first two transmembrane domains with the corresponding region of the Ste2 receptor. The CHI18 receptor has the same Ste2 sequences fused directly to the amino-terminus of the 5HT1a receptor to create a receptor predicted to span the cellular membrane nine times. Bmax values were determined by measuring maximal binding of the radiolabeled ligand 3H-spiperone. Values are given as pmol radioligand bound per mg total protein.

FIGS. 14A, B, C, and D. Growth response of yeast strains exposed to somatostatin is dependent on amount of chimeric G protein expressed. Cultures of yeast strains described in the text are embedded in agar and exposed to the indicated amounts of designated compounds spotted on paper disks placed on top of the agar. Plates are incubated at 30° C.

FIG. 15A, B, C, and D. Growth response of yeast strains exposed to somatostatin is dependent on amount of yeast G protein expressed. Cultures of yeast strains described in the text are embedded in agar and exposed to the indicated amounts of designated compounds spotted on paper disks placed on top of the agar. Plates are incubated at 30° C.

FIGS. 17A, B, C, and D. A mutation in the sst2 gene enhances the growth of yeast cells exposed to somatostatin. Cultures of yeast strains described in the text are embedded in agar and exposed to the indicated amounts of designated compounds spotted on paper disks placed on top of the agar. Plates are incubated at 30° C.

DETAILED DESCRIPTION OF THE INVENTION

Figure 1:
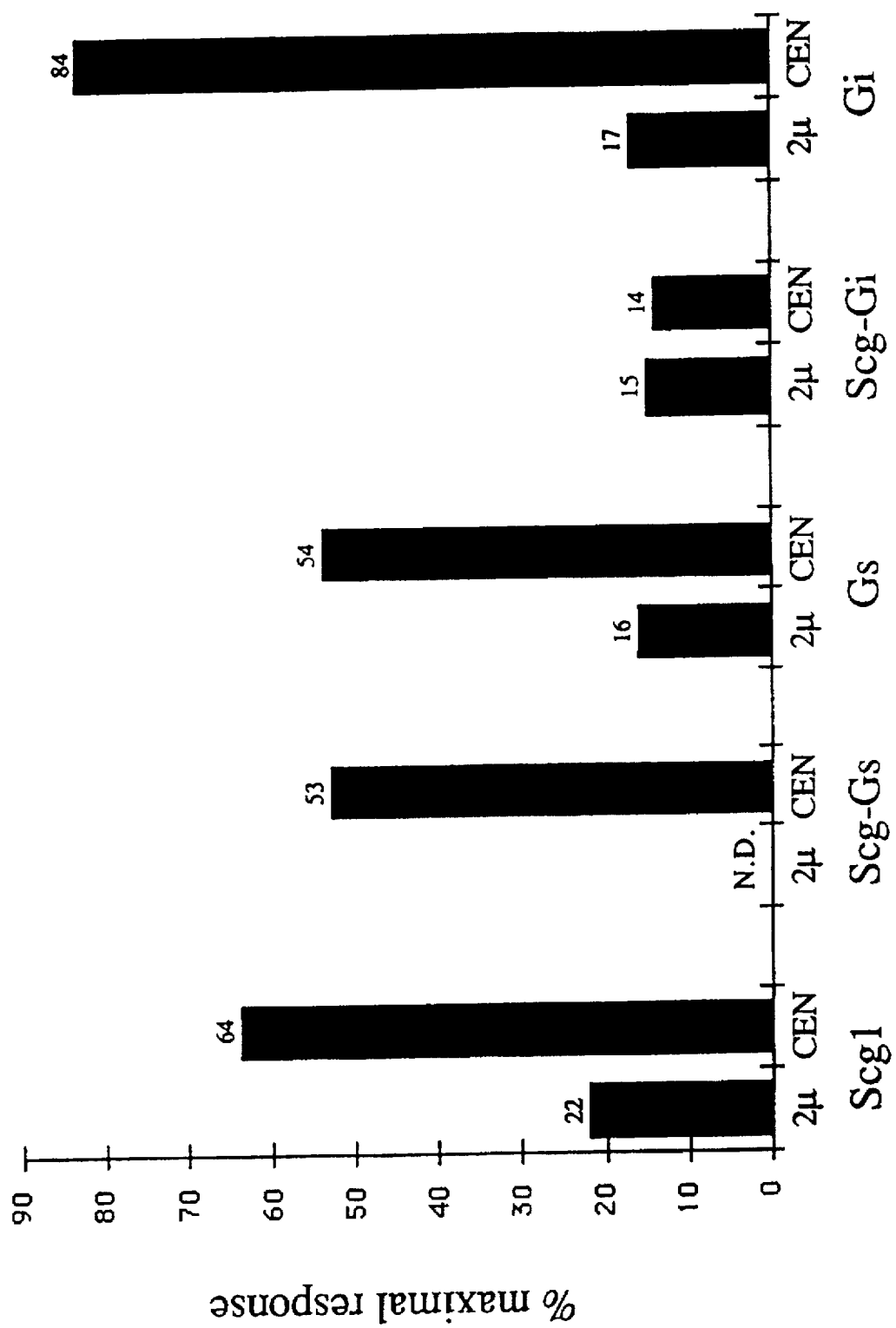
FIG. 1. Strains containing the indicated Gα expression plasmids are treated with mating pheromone (α factor). A measure of resulting signal transduction is provided by a reporter plasmid carrying FUS1-lacZ. Data are represented as a percent of β-galactosidase activity measured in a strain expressing solely the wild type Gα protein.

Nucleotide bases are abbreviated herein as follows:

| A—Adenine | G—Guanine |
|---|---|
| C—Cytosine | T—Thymine |

Amino acid residues are abbreviated herein to either three letters or a single letter as follows:

| Ala;A—Alanine | Leu;L—Leucine |
|---|---|
| Arg;R—Arginine | Lys;K—Lysine |
| Asn;N—Asparagine | Met;M—Methionine |
| Asp;D—Aspartic acid | Phe;F—Phenylalanine |
| Cys;C—Cysteine | Pro;P—Proline |
| Gln;Q—Glutamine | Ser;S—Serine |
| Glu;E—Glutamic acid | Thr;T—Threonine |
| Gly;G—Glycine | Trp;W—Tryptophan |
| His;H—Histidine | Tyr;Y—Tyrosine |
| Ile;I—Isoleucine | Val;V—Valine |

The term "mammalian" as used herein refers to any mammalian species (e.g., human, mouse, rat, and monkey).

The term "heterologous" is used herein with respect to yeast, and hence refers to DNA sequences, proteins, and other materials originating from organisms other than yeast (e.g., mammalian, avian, amphibian, insect, plant), or combinations thereof not naturally found in yeast.

The terms "upstream" and "downstream" are used herein to refer to the direction of transcription and translation, with a sequence being transcribed or translated prior to another sequence being referred to as "upstream" of the latter.

Any G protein-coupled receptor, and the DNA sequences encoding these receptors, may be employed in practicing the present invention. Examples of such receptors include, but are not limited to, adenosine receptors, somatostatin receptors, dopamine receptors, muscarinic cholinergic receptors, α-adrenergic receptors, β-adrenergic receptors, opiate receptors, cannabinoid receptors, growth hormone releasing factor, glucagon, and serotonin receptors. The term receptor as used herein is intended to encompass subtypes of the named receptors, and mutants and homologs thereof, along with the DNA sequences encoding the same.

Any DNA sequence which codes for a Gα subunit (Gα) may be used to practice the present invention. Examples of Gα subunits include Gs subunits, Gi subunits, Go subunits, Gz subunits, Gq, G11, G16 and transducing subunits. G proteins and subunits useful for practicing the present invention include subtypes, and mutants and homologs thereof, along with the DNA sequences encoding the same.

Any DNA sequence which codes for a Gβγ subunits (Gβγ) may be used to practice the present invention. G proteins and subunits useful for practicing the present invention include subtypes, and mutants and homologs thereof, along with the DNA sequences encoding the same.

Any DNA sequence which codes for an adenylylcyclase may be used to practice the present invention. Examples of adenylylcyclase include the product of the D. melanogaster Rutabaga gene and the mammalian subunit types I–VIII [for review see, Tang, W. -J. and Gilman, A. G. (1992) Cell 70, 869–872], and mutants and homologs thereof, along with the DNA sequences encoding the same, which are useful for practicing the present invention.

Any DNA sequence which codes for a G protein-gated potassium channel may be used to practice the present invention. Examples of G protein-coupled potassium channel include GIRK1 [Kubo, Y. Reuveny, E., Slesinger, P. A., Jan, Y. N., and Jan, L. Y. (1993) Nature 364, 802–806], subunits useful for practicing the present invention, and mutants and homologs thereof, along with the DNA sequences encoding the same.

Any DNA sequence which codes for a phospholipase protein may be used to practice the present invention. Examples of phospholipase (PLC) proteins include the D. melanogaster norpA gene product and the PLC-β proteins [for review, see Rhee, S. G., and Choi, K. D. (1992) J. Biol. Chem. 267, 12393–12396], subunits useful for practicing the present invention, and mutants and homologs thereof, along with the DNA sequences encoding the same.

Heterologous DNA sequences are expressed in a host by means of an expression vector. An expression vector is a replicable DNA construct in which a DNA sequence encoding the heterologous DNA sequence is operably linked to suitable control sequences capable of affecting the expression of a protein or protein subunit coded for by the heterologous DNA sequence in the intended host. Generally, control sequences include a transcriptional promoter, an optional operator sequence to control transcription, a sequence encoding suitable mRNA ribosomal binding sites, and (optionally) sequences which control the termination of transcription and translation. Vectors useful for practicing the present invention include plasmids, viruses (including bacteriophage), and integratable DNA fragments (i.e., fragments integratable into the host genome by genetic recombination). The vector may replicate and function independently of the host genome, as in the case of a plasmid, or may integrate into the genome itself, as in the case of an integratable DNA fragment. Suitable vectors will contain replicon and control sequences which are derived from species compatible with the intended expression host. For example, a promoter operable in a host cell is one which binds the RNA polymerase of that cell, and a ribosomal binding site operable in a host cell is one which binds the endogenous ribosomes of that cell.

DNA regions are operably associated when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells of the present invention are cells which have been transformed or transfected with the vectors constructed using recombinant DNA techniques and express the protein or protein subunit coded for by the heterologous DNA sequences. The host cells may express endogenous Gβγ, or may optionally be engineered to express heterologous Gβγ (e.g., mammalian) in the same manner as they are engineered to express heterologous Gα. A variety of yeast cultures, and suitable expression vectors for transforming yeast cells, are known. See e.g., U.S. Pat. No. 4,745,057; U.S. Pat. No. 4,797,359; U.S. Pat. No. 4,615,974; U.S. Pat. No. 4,880,734; Pat. No. 4,711,844; and U.S. Pat. No. 4,865,989. *Saccharomyces cerevisiae* is the most commonly used among the yeasts, although a number of other yeast species are commonly available. See. e.g., U.S. Pat. Nos. 4,806,472 (*Kluveromyces lactis* and expression vectors therefore); 4,855,231 (*Pichia pastoris* and expression vectors therefore). Yeast vectors may contain an origin of replication from the endogenous 2 micron yeast plasmid or an autonomously replicating sequence (ARS) which confers on the plasmid the ability to replicate at high copy number in the yeast cell, centromeric (CEN) sequences which limit the ability of the plasmid to replicate at only low copy number in the yeast cell, a promoter, DNA encoding the heterologous DNA sequences, sequences for polyadenylation and transcription termination, and a selectable marker gene. An exemplary plasmid is YRp7, (Stinchcomb et al., (1979) Nature 282, 39; Kingsman et al., (1979) Gene 7, 141; Tschemper et al., (1980) Gene 10, 157]. This plasmid contains the TRP1 gene, which provides a selectable marker for a mutant strain of yeast lacking the ability to Grow in the absence of tryptophan, for example ATCC No. 44076. The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase [Hitzeman et al., (1980) J. Biol. Chem. 255, 2073] or other glycolytic enzymes [(Hess et al., (1968) J. Adv. Enzyme Reg. 7, 149]; and Holland et al., (1978) Biochemistry 17, 4900], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, trioseposphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphates, degradative enzymes associated with nitrogen metabolism, and the aforementioned metallothionein and glyceraldehyde-3-phosphate dehydrogenase, as well as enzymes responsible for maltose and galactose utilization. Finally, in constructing suitable expression plasmids, the termination sequences associated with these genes may also be ligated into the expression vector 3' of the heterologous coding sequences to provide polyadenylation and termination of the mRNA.

A novel DNA expression vector described herein which is useful for carrying out the present invention contains a first segment comprising yeast DNA sequences upstream of the translational initiation site of the heterologous DNA sequences and a second segment downstream from said first segment and in correct reading frame therewith, the second segment comprising a DNA sequence encoding a heterologous G protein-coupled receptor. Such adaptations of the translational initiation site may enhance expression of a heterologous protein. Additionally, a first segment comprising yeast DNA sequences comprising at least a fragment of the extreme amino-terminal coding sequence of a yeast G protein-coupled receptor and a second segment downstream from said first segment and in correct reading frame therewith, the second segment comprising a DNA sequence encoding a heterologous G protein-coupled receptor. The gene sequences encoding yeast pheromone receptors may be used primarily as an epitope tag for detecting expression of the receptors using antibodies directed specifically to the epitope sequence. In constructing such a vector, a fragment of the extreme amino-terminal coding sequence of the heterologous G protein-coupled receptor may be deleted. The first and second segments are operatively associated with a promoter, such as the GAL1 promoter, which is operative in a yeast cell. Coding sequences for yeast G protein-coupled receptors which may be used in constructing such vectors are exemplified by the gene sequences encoding yeast pheromone receptors (e.g., the STE2 gene, which encodes the α-factor receptor, and the STE3 gene, which encodes the α-factor receptor). The levels of expression obtained from these novel vectors may be enhanced if at least a fragment of the 5'-untranslated region of a yeast gene is positioned upstream from the first segment and operatively associated therewith, however, such sequences are not necessary for expression of G protein-coupled receptors in yeast.

Any of a variety of means for detecting the dissociation of Gα from Gβγ can be used in connection with the present invention. The cells could be disrupted and the proportion of these subunits and complexes determined physically (i.e., by chromatography). The cells can be disrupted and the quantity of Gα present assayed directly by assaying for the enzymatic activity possessed by Gα in isolation (i.e., the ability to hydrolyze GTP to GDP). Since whether GTP or GDP is bound to the G protein depends on whether the G protein exists as a Gβγ or Gαβγ complex, dissociation can be probed with radiolabelled GTP. As explained below, morphological changes in the cells can be observed.

A particularly convenient method for detecting ligand-binding to heterologous receptor expressed in yeast cells is to provide in the cells a third heterologous DNA sequence, comprising a pheromone-responsive promoter and an indicator gene positioned downstream from the pheromone-responsive promoter and operatively associated therewith. With such a sequence in place, the detecting step can be carried out by monitoring the expression of the indicator gene in the cell. Any of a variety of pheromone responsive promoters could be used, examples being the BAR1 gene promoter and the FUS1 gene promoter. Likewise, any of a broad variety of indicator genes could be used, with examples including the HIS3, G418r, URA3, LYS2, CAN1 and LacZ genes. Furthermore, signals transduced through heterologous G proteins may be detected by coexpressed heterologous effector proteins. For example, 1) ligand-dependent stimulation of a heterologous adenylylcyclase may permit a yeast strain lacking its own adenylylcyclase due to mutation in the cdc35 gene to survive, 2) ligand-dependent stimulation of a heterologous G protein-coupled potassium channel may permit a yeast strain unable to grow in medium containing low potassium concentration [(trk1, trk2), for example, see Anderson, J. A. et al (1992) Proc. Natl. Adad. Sci. U.S.A 89, 3736–3740] to survive, or (3) ligand-dependent stimulation of a heterologous PLC-β may permit a yeast strain lacking its own PLC [(plc1), for example, see Payne, W. E. and Fitzgerlad-Hayes, M. (1993) Mol. Cell. Biol. 13, 4351–4363] to survive.

A yeast expression system is described here wherein yeast cells bearing SSTR and chimeric G-protein are dependent upon the presence of somatostatin for continued growth. As noted above, transformed host cells of the present invention express the proteins or proteins subunit coded for by the heterologous DNA sequences. When expressed, the G protein-coupled receptor is located in the host cell membrane (i.e., physically positioned therein in proper orientation for both the stereoselective binding of ligands and for functional interaction with G proteins on the cytoplasmic side of the cell membrane). The ability to control the yeast pheromone response pathway by expression of a heterologous receptor and its cognate G protein subunit has the potential to facilitate structural and functional characterization of heterologous G protein-coupled receptors. By scoring for responses such as ligand-dependent growth or induction of a reporter gene e.g. β-galactosidase $^{O2}HIS^3$, the functional properties of mutant receptors can now be rapidly tested. Similarly, as additional genes for putative G protein-coupled receptors are isolated, numerous ligands can be screened to identify those with activity toward previously unidentified receptors. Moreover, novel ligands that functionally interact with any receptor thus expressed can be identified.

The following Examples are provided to further illustrate various aspects of the present invention. They are not to be construed as limiting the invention.

EXAMPLE 1

Functional Expression of Mammalian Gα Proteins in *Saccharomyces cerevisiae*

Sensitive bioassay is utilized to measure interference of yeast Gα-Gβγ interactions by expression of heterologous Gα proteins. Mammalian Gα genes are expressed from 2μ or centromere-bearing plasmids under the control of the constitutive PGK or the inducible CUP1 promoter. The data demonstrate that the rat Gαs, $G_{αi2}$, and chimeric yeast/mammalian Gα can effectively interact with yeast Gβγ.

Media and Strains

Growth of bacterial strains and plasmid manipulations are performed by standard methods (Maniatis T., Molecular Cloning. Cold Spring Harbor Laboratory Press, 1982). Growth and transformation of yeast strains are performed as described in Rose et al. (Rose M. D., Methods in yeast genetics, Cold Spring Harbor Laboratory Press, 1990). The yeast strains used in these studies (CY414; MATa ura3–52 trp1 leu2 his3 pep4::HIS3) originate from strains described by E. Jones (Jones, E. W., Ann. Rev. Genet 18:233, 1984). CY414 is sequentially transformed with the FUS1-lacZ fusion plasmid pSB234 (Trueheart J., et al Mol. Cell. Biol., 7(7): 2316–2328, 1987) and Gα expression plasmids.

Construction of Gα Expression Plasmids

Rat cDNA clones for Gαs and $G_{αi2}$ and for fusions with the yeast SCG1 gene are described elsewhere [Kang, Y. -S., Kane, J., Kurjan, J., Stadel, J. M., and Tipper, D. J. (1990) Mol. Cell. Biol. 10, 2582–2590]. To express these genes from low-copy-number plasmids, XhoI–SalI fragments containing each expression cassette (including the PGK promoter and terminator sequences) are isolated and cloned into the CEN plasmid pRS414 digested with XhoI. For inducible expression, the DNA segment containing PGK promoter sequences are replaced with upstream activating sequences form the CUP1 gene.

β-galactosidase Assays.

Cultures are diluted to $5×10_7$ cells/ml and aliquotted into separate tubes. Pheromone is added to a final concentration of $10^{-9}M$ to one sample. Cultures are then incubated for 4 hrs at 30° C. Subsequent measurement of β-galactosidase activity is conducted as described elsewhere (Rose M. D., Cold Spring Harbor Laboratory Press, 1990).

High and low-copy-number plasmids carrying the yeast SCG1 or mammalian Gαs or Gαi or chimeric yeast/mammalian Gα genes expressed from the yeast PGK promoter are transformed into a wild-type yeast strain also containing a plasmid carrying a FUS1-lacZ gene fusion. Expression of the FUS1 gene is stimulated in response to receptor activation by binding of pheromone. Therefore, signal transduction can be quantitated by measuring β-galactosidase activity generated from the FUS1-lacZ reporter gene. Interference of normal signal transduction by expression of an heterologous Gα protein is observed as a decrease in β-galactosidase activity.

Strains expressing introduced Gα genes are assayed for pheromone-induced gene activation. Data are represented as percent of wild-type response in FIG. 1. Expression from all Gα plasmids reduced FUS1-lacZ expression levels demonstrating that the Gα proteins functionally coupled to yeast Gβγ. A dose dependence was observed for Scg1, Gαs and Gαi. Expression from high-copy-number plasmids greatly reduces signaling suggesting that a large excess of heterologous Gα protein is present. The Scg-Gαi chimeric protein reduces signaling to near the unstimulated background levels even from the low-copy-number plasmid. Other CEN expression plasmids reduce signalling to 53 to 84% of wild-type levels.

Figure 2:
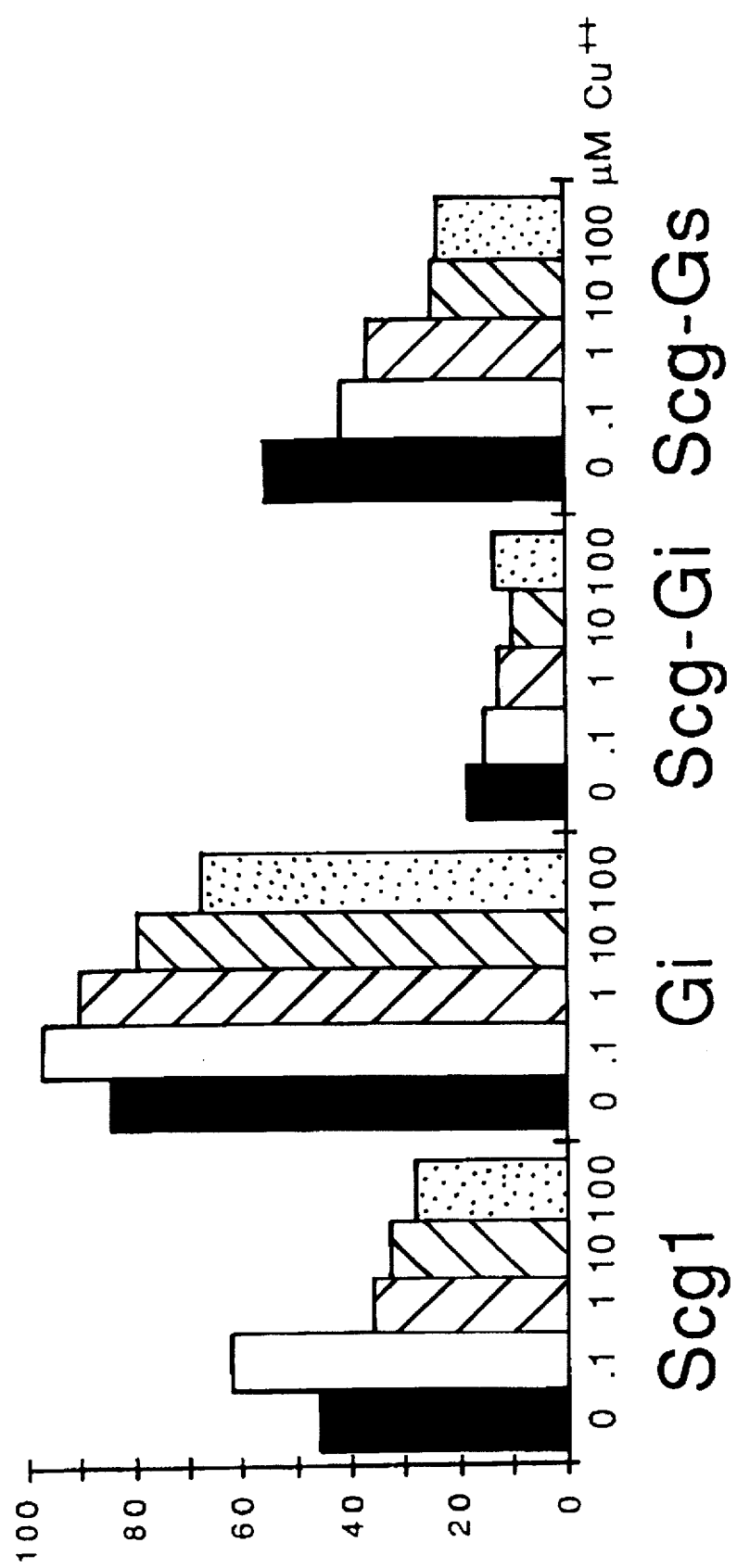
FIG. 2. Strains containing the indicated CUP1p-Gα expression plasmid and grown in medium containing the indicated concentration of copper are treated with mating pheromone (α factor). A measure of resulting signal transduction is provided by a reporter plasmid carrying FUS1-lacZ. Data are represented as a percent of β-galactosidase activity measured in a strain expressing no exogenous Gα protein.

To achieve more precise control of Gα expression and reduce expression to a level sufficiently low that minimal effects on pheromone induced signaling will occur, Gα genes (except Gαs) are placed under the control of the inducible CUP1 promoter and transformed into yeast on low-copy-number plasmids. The level of signaling repression mediated by these plasmids is dependent on the concentration of Cu++4 added to the medium (FIG. 2). However, basal expression (no Cu++4 added) was equivalent to levels observed from the PGK promoter (FIG. 1). As in the previous experiment, the SCG-Gαi chimeric protein reduces signaling to almost background levels.

The data presented in FIGS. 1 and 2 indicates that all Gα expression plasmids examined produce functional Gα proteins in that all inhibit the signal transduction pathway. Using a constitutive promoter (PGK), most Gα genes exhibit a dose-dependent effect with high-copy-number 2 micron plasmids drastically reducing signaling (FIG. 1).

Lower expression from CEN plasmids reduce signaling levels as little as 16% (Gs; FIG. 1). Disruption of signal transduction by Scg-Gαi, even from a low-copy-number plasmid, suggests that this chimeric Gα protein impairs activity. This is also observed in the CUP1 expression experiments and is consistent with a kinetic shift to the GDP bound structure. Expression of the other Gα genes from the CUP1 promoter shows expected dose/response effects with reduced signaling correlated to increased Cu++ concentrations (FIG. 2).

EXAMPLE 2

Pharmacological Evaluation of Heterologous G Protein-coupled Receptors Expressed in *Saccharomyces cerevisiae* Yeast Strains Growth and transformation of yeast strains are performed as described (Rore, M. D., Methods in Yeast Genetics, Cold Spring Harbor Laboratory Press, 1990). The yeast strains used in these studies (CY414; MATa ura3–52 trp1 leu2 his3 pep4ΔHIS3) originate from strains described by E. Jones (Jones, E. W., Ann. Rev. Genet, 18:233, 1984).

Nucleic acid manipulation. Growth of bacterial strains and plasmid manipulations are performed by standard methods [Sambrook, J., Fritsch, E. F., and Maniatis, T., Molecular Cloning, 2nd ed. (Cold Spring Harbor Laboratory Press, 1989)]. DNA sequencing is performed by high temperature cycle sequencing (Applied Biosystems).

Protein analysis. Receptor expression strains are grown in synthetic complete medium lacking specific nutrients to select for plasmid retention and containing 3% galactose to induce receptor gene expression. Cells are pelleted and washed in lysis buffer (1 mM sodium bicarbonate, pH 7.2, mM EGTA, 1 mM EDTA) then resuspended in lysis buffer plus protease inhibitors (5 µg/ml leupeptin, 10 µg/ml benzamidine, 10 µg/ml Bacitracier, 5 µg/ml pepstatin, 5 µg/ml aprotinin) and lysed by physical disruption with glass beads. Debris is removed by centrifugation at 1000×g for 10 min. The membrane fraction is isolated by centrifugation at 100,000×g for 10 min. This pellet is washed once in lysis buffer plus inhibitors. Polyacrylamide gel electrophoresis of yeast extracts is performed by standard methods except without boiling of samples. Proteins are transferred to Immobilon-P millipore filters by the semi-dry technique. Receptor protein is visualized using ECL reagents with rabbit anti-Ste2 antibodies.

Radioligand binding assays. Reactions are performed in a volume of 0.2 µl with 5 to 50 µg of protein. Binding assays for 5HT1a receptor or β2-adrenergic receptor ligands uses a buffer of 50 mM Tris, pH 7.4, 10 mM MgC$_{12}$. Somatostatin binding is performed in a buffer of 50 mM HEPES, pH 7.4, 5 mM MgC$_{12}$. After allowing ligand binding to reach equilibrium at room temperature, membrane fractions are isolated on GFC glass fiber filters. The following final concentrations of ligands are used: radioligands-$^3$H-spiperone, 80 nM; $^{125}$I-cyanapindolol, 250 pM; $^{125}$I-tyr11-somatostatin 14, 250 pM; competitors-serotonin, 10 µM; propranolol, 20 µM, somatostatin14, µM. The guanosine triphosphate analog Gpp(NH)p is used at 100 µM.

Figure 3:
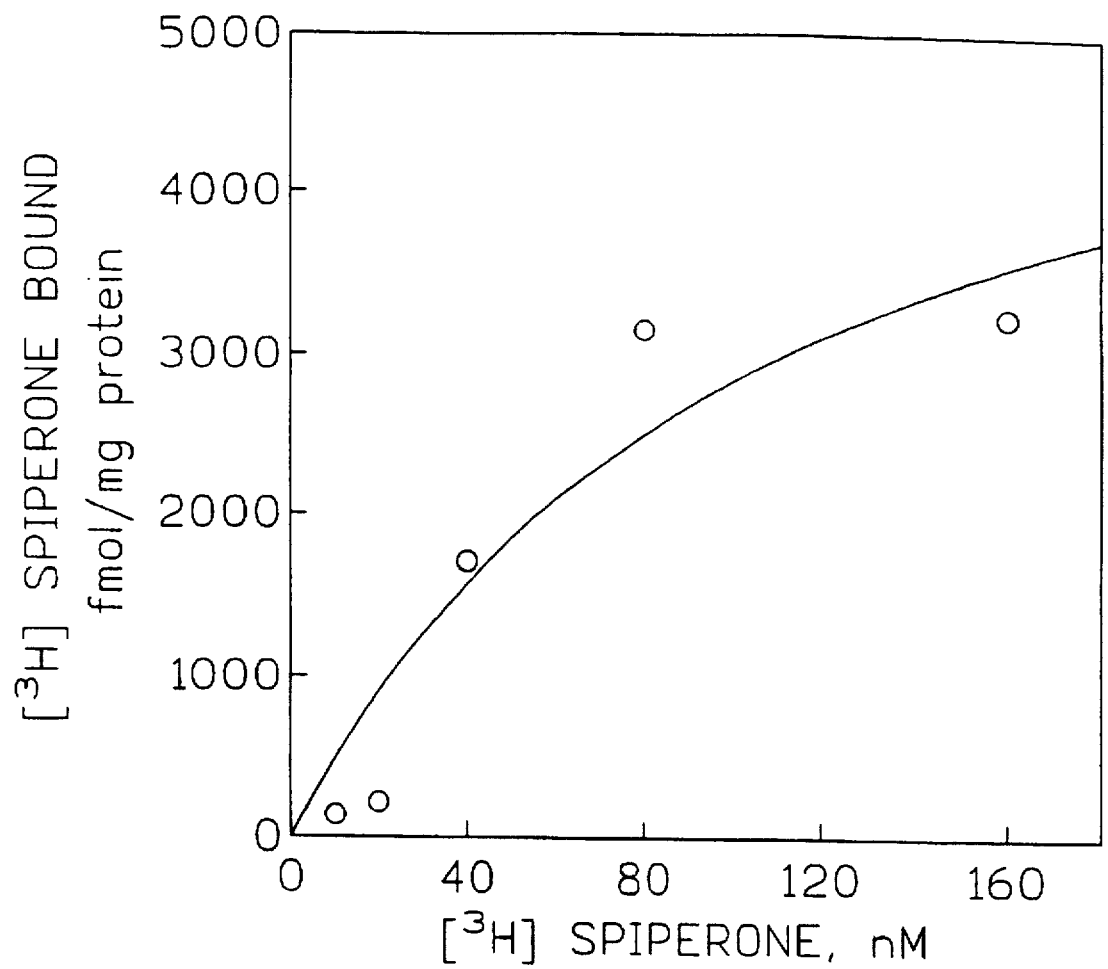
FIG. 3. Saturation binding of 3H-spiperone to yeast membrane fractions prepared from a strain (CY382) expressing the 5HT1a serotonin receptor. Bmax=3.2 pmol/mg protein; Kd=115 nM.

Expression of the human 5HT1a serotonergic receptor. The gene encoding the human 5HT1a receptor is modified to add the first 14 amino acids of the yeast Ste2 protein and cloned into the expression plasmid pMP3. The resultant plasmid, designated pCHI11, is transformed into a yeast strain devoid of endogenous receptor (Ste2) but otherwise wild-type. This strain, designated CY382, is grown in medium containing galactose to induce receptor expression, fractioned and tested for receptor activity by binding of the radiolabelled antagonist $^3$H-spiperone. Saturation binding demonstrates that the receptor is expressed at high levels (Bmax=3.2 pmol/mg protein) and that it binds spiperone with an affinity (Kd=115 nM; FIG. 3) similar to that observed in mammalian tissues (Kd=20 to 100 nM).

Two chimeric receptor genes are engineered; in pCHI17, sequences encoding the N-terminus including the first two transmembrane domains of the 5HT1a receptor are replaced with the corresponding sequences of the Ste2 receptor, and in pCHI18, these Ste2 sequences are added directly to the N-terminus of the 5HT1a receptor to create a novel nine-transmembrane-domain receptor (FIG. 4). Strains expressing these receptors are examined for binding of radiolabelled ligand. Both receptors demonstrate specific binding of the 5HT receptor antagonist spiperone (FIG. 4). Replacement of the first two transmembrane domains with those of an unrelated receptor does not apparently affect binding of this ligand. Addition of transmembrane domains do not effect binding suggesting that this unusual receptor can attain a functional conformation in the cell membrane. Strains carrying pCHI11, pCHI17, or pCHI18 produce Bmax values of 3.1, 1.6 or 0.7 pmol/mg, respectively. Although these chimeric receptors produce interesting results regarding receptor structure, they do not enhance overall levels of functional receptors in the cell.

All intracellular sequences of the 5HT1a receptor are replaced with corresponding sequences of the yeast Ste2 protein to directly couple the receptor to the yeast G protein. The resultant chimeric receptor, CHI16, is expressed in a wild-type yeast strain and examined for high affinity binding of 5HT1a receptor agonists. Agonist binding is not detected. However the level of radiolabelled spiperone binding is equal to CHI11 indicating that this receptor is expressed at high levels and in a functional conformation.

Figure 5:
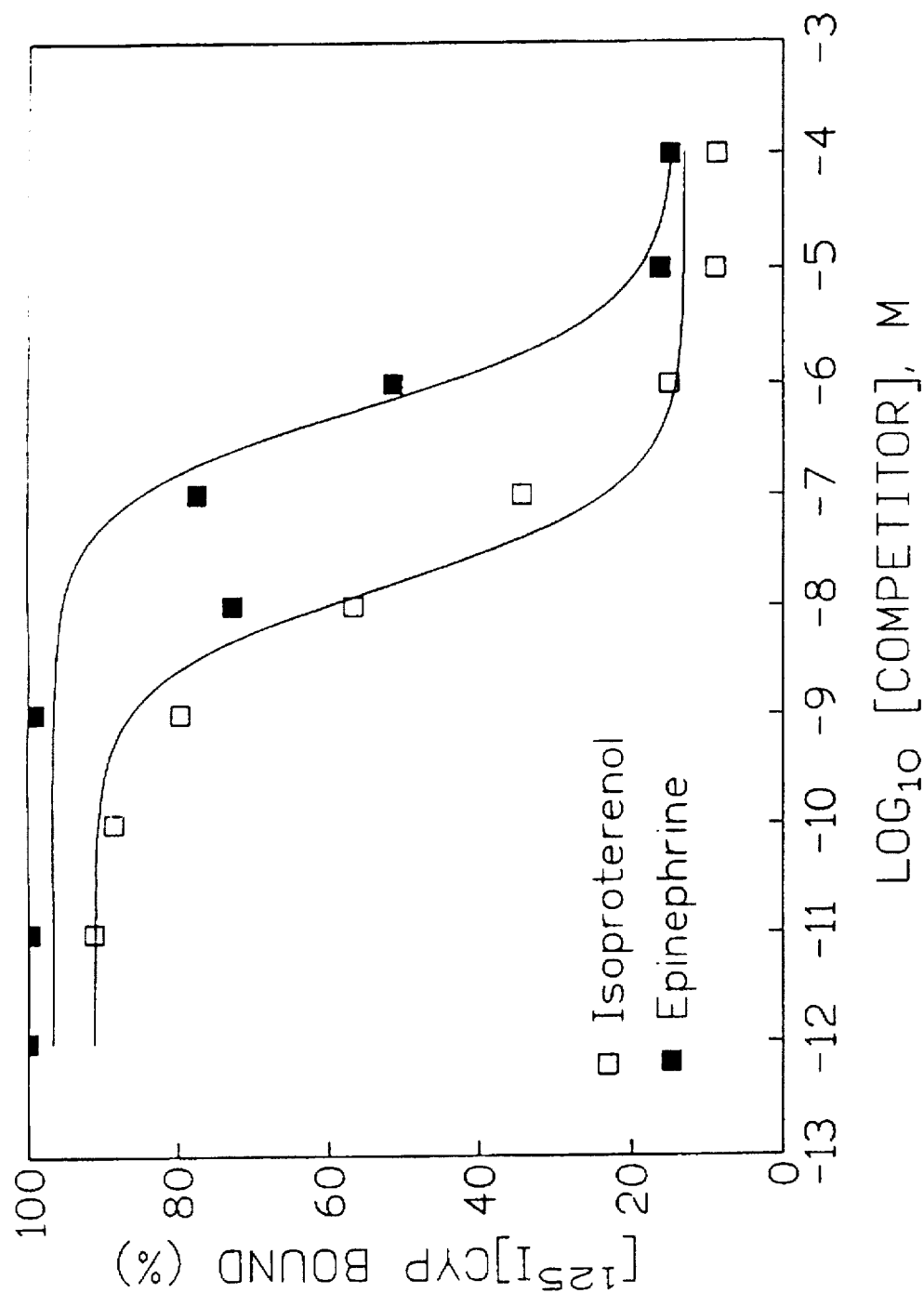
FIG. 5. Competition binding analysis of the agonists isoproterenol or epinephrine against $^{125}$I-cyanopindolol with crude membrane extracts prepared from a wild-type yeast strain expressing the β2-adrenergic receptor. Data are presented as percent maximal radioligand binding. IC50 values=10 nM, isoproterenol; 200 nM, epinephrine.
Figure 6:
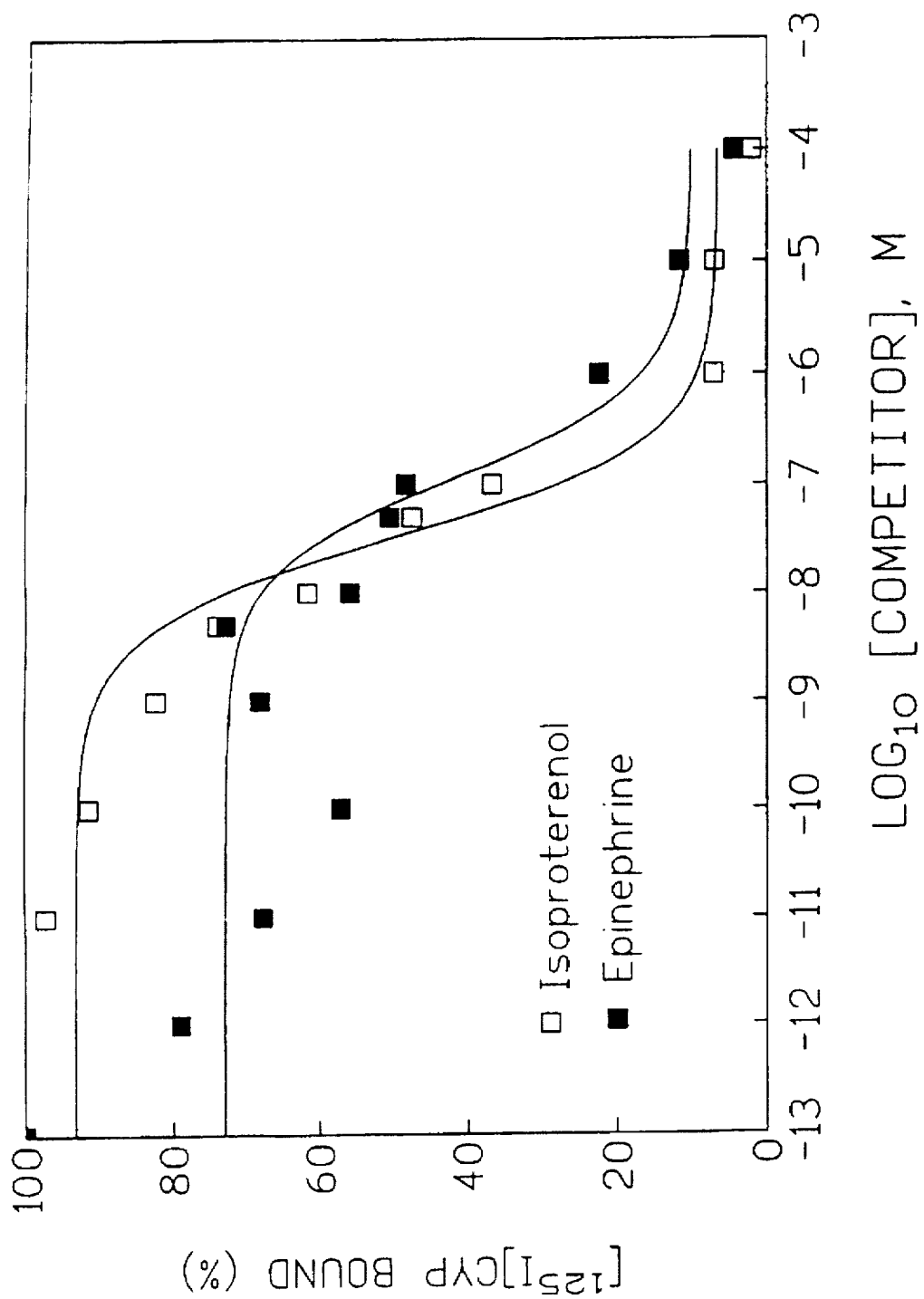
FIG. 6. Competition binding analysis of the agonists isoproterenol or epinephrine against $^{125}$I-cyanopindolol with extracts prepared from a yeast strain coexpressing the β2-adrenergic receptor and mammalian Gαs. Data are presented as percent maximal radioligand binding. IC$_{50}$ values= 10 nM, isoproterenol; 60 nM, epinephrine.

Expression of the human β2-adrengeric receptor. The human β2-adrenergic receptor is expressed in yeast with the intention of using it as a model to optimize expression and G protein coupling. A yeast strain expressing the receptor is examined by Scatchard analysis for binding of the ligand $^{125}$I-cyanopindolol. Binding is saturable and demonstrated a Kd (23 pM) similar to that reported in mammalian tissues. Strains with or without coexpressed Gαs is then examined in competition assays in which binding of this radioligand is competed with the agonists isoproterenol or epinephrine. High affinity binding, which is only expected to occur if the receptor is actively coupled to G protein, was observed in both strains (FIGS. 5 and 6). The extrapolated Ki values for these ligands (isoproterenol=10 nM; epinephrine=60 nM) are consistent with affinities observed in mammalian tissues and exhibit the expected order of potency. However, other data suggest that the high affinity binding of agonists to the β2-adrenergic receptor in yeast is anomalous and not a result of coupling to G protein. In particular, the third intracellular loop (containing the primary Gα contact points) of the β2-adrenergic receptor is replaced with the corresponding domain of the yeast Ste2 receptor. This receptor exhibits the same affinities for V8.3 2-adrenergic agonists suggesting that the β2-adrenergic receptor takes on an inappropriate conformation in yeast.

Figure 7:
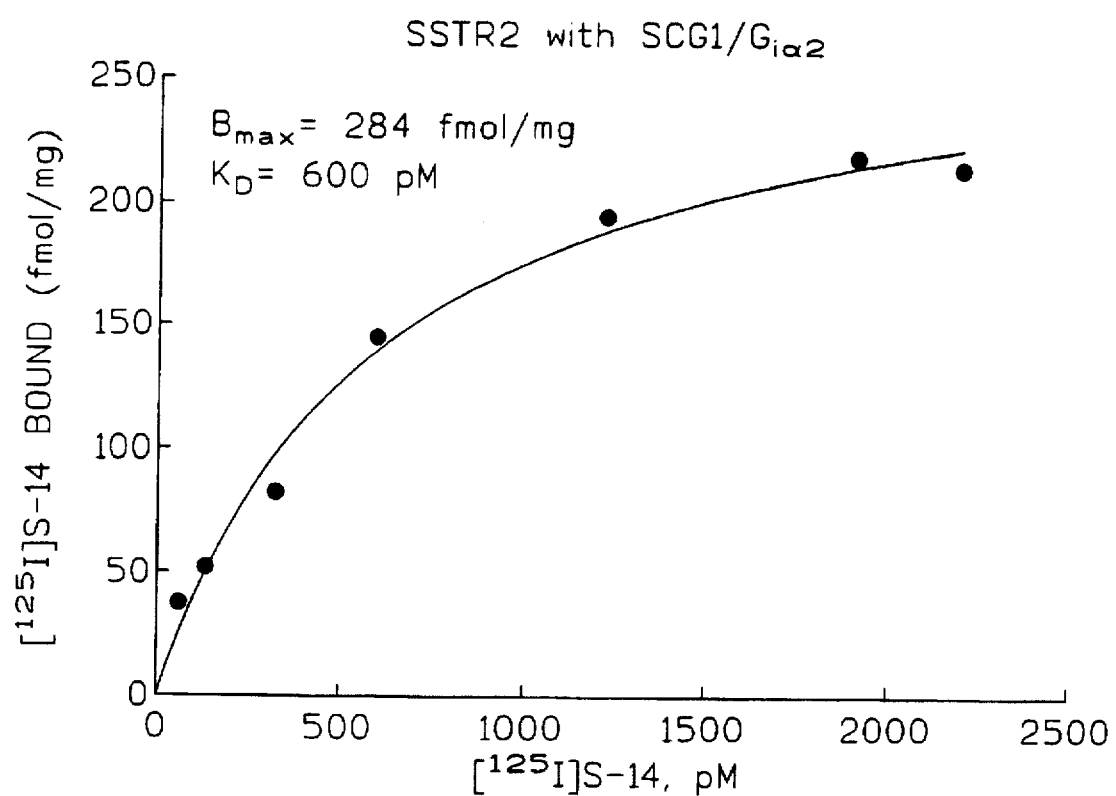
FIG. 7. Saturation binding of [$^{125}$I]tyr$^{11}$S-14 to membranes of yeast cells coexpressing the SSTR2 subtype and Scg1/G$_{i\alpha2}$. Membranes from yeast cells expressing the SST2 subtype were prepared as described in *Experimental Procedures*. Saturation binding was performed with 20–1600 pM [$^{125}$I]tyr$^{11}$S-14 (10 μM cold S-14 ranged from 10 to 40%. Displayed is a representative experiment performed in duplicate.
Figure 8:
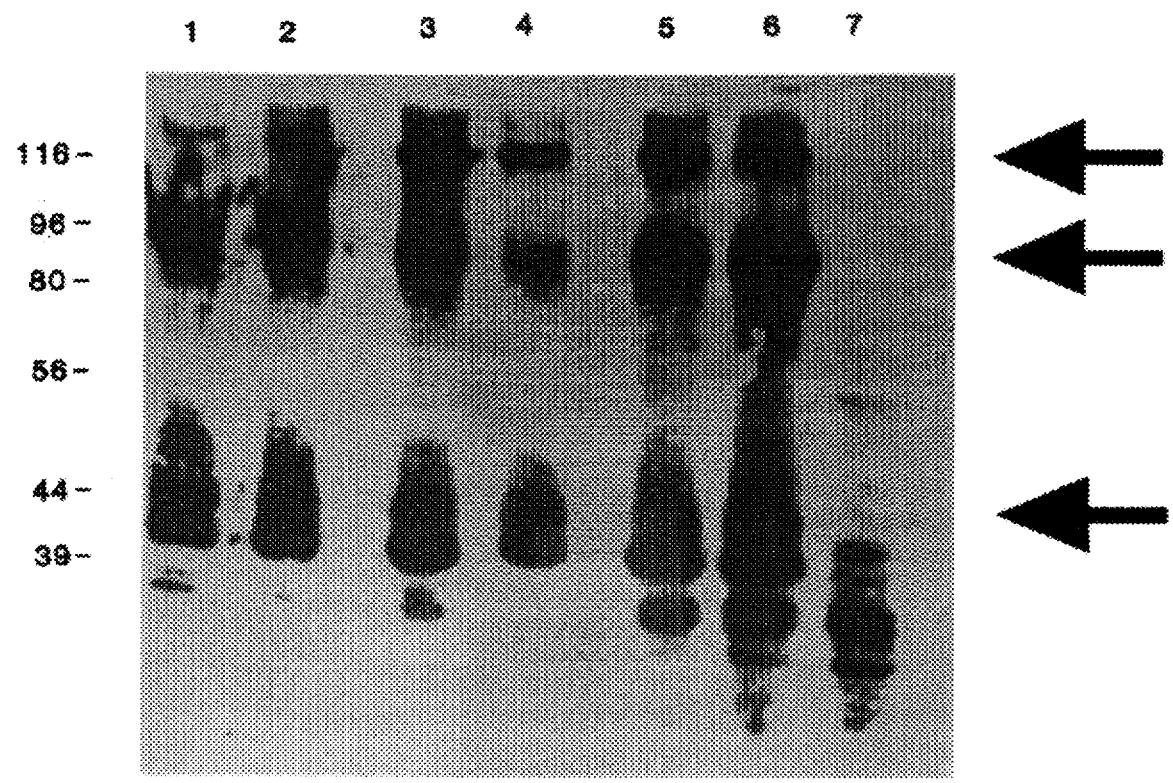
FIG. 8. Immunoblot showing somatostatin receptor expression. Membrane fractions are isolated from the indicated yeast strains. Aliquots of 5 to 30 μg of protein are examined by polyacrylamide gel electrophoresis/Western blot analysis. Molecular weight markers are indicated in kilodaltons. Arrows mark somatostatin receptor protein bands. Several species of this receptor are observed; doublet and triplet bands in addition to the 43 kd single receptor. Lanes, 1+2, CY602 (see Table 1); 3+4, CY603; 5+6, CY624; 7, congenic strain expressing no receptor.
Figure 9:
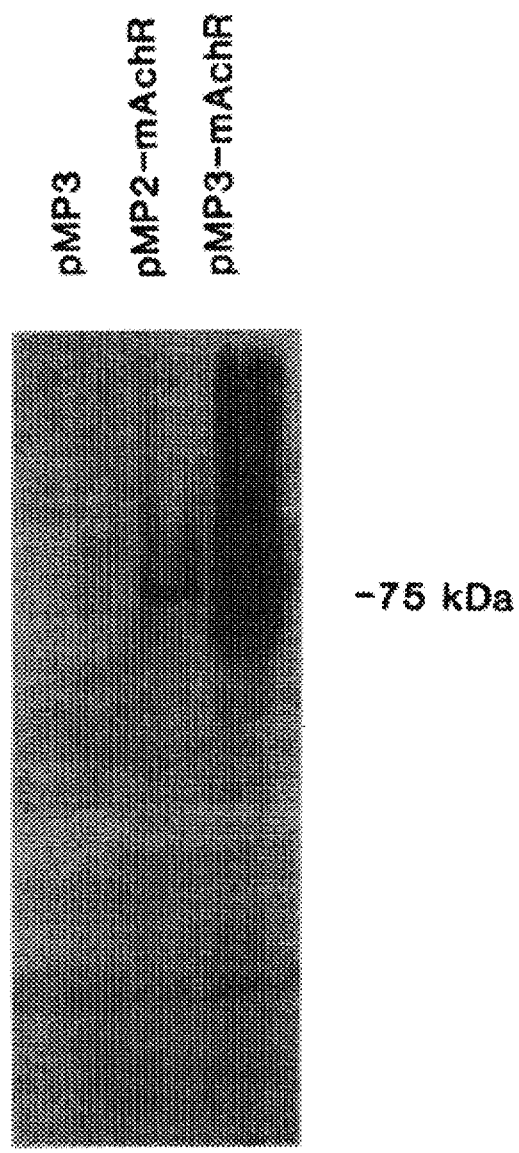
FIG. 9. Immunoblot showing muscarinic acetylcholine receptor (mAchR) expression. Membrane fractions are isolated from the indicated yeast strains. Aliquots of 30 μg of protein are examined by polyacrylamide gel electrophoresis/ western blot analysis as described in the text. Molecular weight markers are indicated in kilodaltons. Arrows mark mAchR protein bands.

Expression of rat somatostatin receptor. High affinity binding of somatostatin to SSTR2 is dependent on formation of a receptor/G protein complex (Strnad et al, 1993). When SSTR2 and G protein are uncoupled from each other high affinity binding of [$^{125}$I]tyr$^{11}$S-14 is attenuated. As shown in FIG. 7, binding of [$^{125}$I]tyr$^{11}$S-14 to SSTR2 expressed in yeast coexpressing Scg1/G$_{αi2}$ is saturable and of high affinity. The calculated $K_d$ of [$^{125}$I]tyr$^{11}$S-14 binding SSTR2 expressed in yeast is 600 pM. Similar binding affinities are observed when $G_{\alpha i2}$ is coexpressed with SSTR2 rather than Scg1/$G_{\alpha i2}$. The d observed in yeast is in close agreement to the calculated $K_d$ of [$^{125}$I]tyr$^{11}$S-14 binding of SSTR2 expressed in mammalian cells (Strnad et al., 1993). It is demonstrated that addition to the N-terminus of the yeast Ste2 receptor to this receptor has no affect on its ability to bind S-14. The Ste2 sequences act as a tag for immunochemical examination of receptor expression. The immunoblot shown in FIG. 7 illustrates the high level of expression SSTR2 in three different strains. Yeast strains expressing the SSTR2 somatostatin receptor and different Gα proteins are derived from strain YPH500. These strains share the genotype MATa scg1ΔhisG lys2-801 ura3–52 leu2Δ1 trp1Δ63 his3Δ200 ade2 SSTR2. Strains designated CY624 (Gαi), CY602 (Gαs, and CY603 Scg1) are examined for specific binding of radiolabelled somatostatin-14 (S-14). All three exhibit some degree of somatostatin binding (Table 1). High affinity binding of this ligand requires coupling of the receptor to G protein, normally Gαi (Luthin D. R. 1993; Strnad J. 1993), so the high level of binding in the absence of Gαi is unexpected. As confirmation that the receptor is coupled to G proteins, binding is examined in the presence of the nonhydrolyzable guanosine triphosphate analog Gpp(NH)p. The addition of this compound eliminates ligand binding (Table 1) demonstrating that the SSTR2 receptor is coupled to G protein. These data demonstrate that a mammalian G protein-coupled receptor can functionally interact with a G protein composed of its favored Gα protein plus yeast Gβ and Gγ subunits and that a heterologous receptor can functionally couple to a G protein entirely composed of yeast subunits.

TABLE 1

| Binding of $^{125}$I-somatostatin$^a$ | | | |
|---|---|---|---|
| STRAIN | Gα | Bmax$^b$ | +Gpp(NH)pc$^c$ |
| CY624 | Gαi | 94.5 | 22% |
| CY602 | Gαs | 13.7 | 0% |
| CY603 | Scg1 | 24.7 | 4% |

$^a$Crude membrane extracts were prepared from yeast strains expressing the rat SSTR2 somatostatin receptor subtype and the indicated Gα protein. The maximal binding of radiolabeled somatostatin 14 was measured as described in the text.
$^b$Bmax values are given as fmol/mg total protein.
$^c$The non-hydrolyzable GTP analog Gpp(NH)p was added to samples to uncouple receptor and G protein. Data are presented as percent radioligand bound compared to untreated samples.

Expression of Drosophila muscarinic acetylcholine receptor. DNA sequences encoding a Drosophila muscarinic acetylcholine receptor (Dm mAChR) are modified by addition of a SalI site in the 5' coding sequences through the use of PCR. DNA sequences encoding the first 23 amino acids of the STE2 gene product are added to the 5' end of Dm mAChR as a BamHI/SalI fragment. The modified Dm mAChR is inserted into the BamHI site in plasmid pMP3, placing expression of the receptor under the control of the GAL1 promoter, forming plasmid pMP3-Dm mAChR. Strain CY414 is transformed with this plasmid and cultured for receptor expression by standard methods. Crude membrane preparations are prepared from these cells and tested for the presence of specific binding sites for the muscarinic antagonist 3H-quinuclidinyl benzilate (10 nM) competed with atropine (50 μM). Specific binding sites (Bmax 10 and 30 fmol/mg) are observed.

Drosophila mAchR expression is also detectable by immunoblotting methods. An abundant 75 kDa polypeptide, consistent with the predicted molecular weight from the primary sequence of mAchR, is detected in samples of protein (30 μg/lane) form crude membrane preparations from cells expressing mAchR from pMP3 using an antibody directed against the associated Ste2 epitope. Substantially less protein is detected when mAchR is expressed from pMP2, a derivative of pMP3 lacking GAL3 sequences, which is not expected to confirm high level expression of mAchR.

Expression of an α2-adrenergic receptor (α2-AR). An EcoRI-NarI fragment from plasmid pMP3, including the GAL1,10 promoter EcoRI-BamHI fragment, DNA sequences encoding the first 23 amino acids of the STE2 gene product present on a BamHI-SalI fragment, SalI-SphI polylinker fragment from YEp352, and STE7 terminator sequences, is transferred to pRS424, forming pLP15. A PstI-PvuII fragment encoding a porcine α2A-AR [Guyer, C. A., Horstman, D. A., Wilson, A. L., Clark, J. D., Cragoe, E. J., and Limbird, L. E. (1990) J. Biol. Chem. 265, 17307–17317] is inserted into the PstI-SmaI sites of pLP15, forming pLP50. An EcoRI fragment of GAL4 is inserted into the EcoRI site of pLP50, forming pLP60. Strain LY124 [a deriviative of YPH500 (Stratagene) containing the scg1ΔhisG allele and bearing plasmid pLP10 [pLP10:pUN75 (Elledge, S. J. and Davis, R. W. Genetics 87, 189–194) containing the PGK-Scg1-Gαi2 XhoI-SalI fragment from pPGKH-Scg1Gαi2 inserted into the SalI site] is transformed with pLP60 and cultured for receptor expression by standard methods. Crude membrane preparations are prepared from these cells and tested for the presence of specific binding sites for the α2-AR antagonist 3H-rauwolscine (200 nM) competed with phentolamine (10 μM). Specific binding sites with a Bmax of between 10 and 84 fmol/mg were observed.

Porcine α2AR expression is also detectable by immunoblotting methods. Several abundant polypeptides are detected in samples of protein 30 μg/lane) from crude membrane preparations from cells expressing α 2AR from pMP3 using an antibody directed against the associated Ste2 epitope.

EXAMPLE 3

Figure 10:
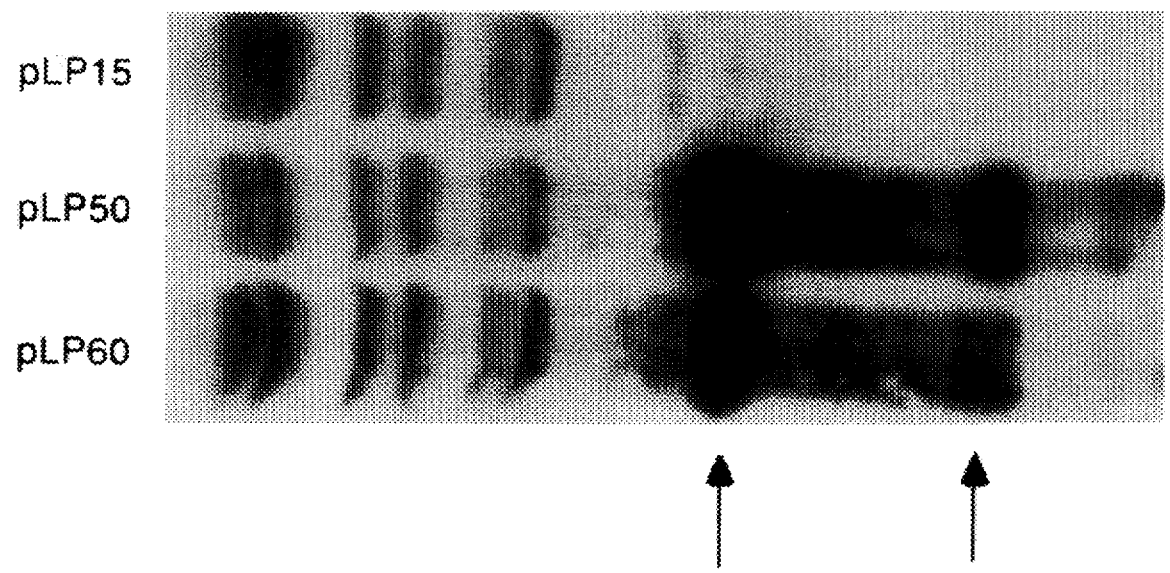
FIG. 10. Immunoblot showing α2-AR expression. Membrane fractions are isolated from the indicated yeast strains. Aliquots of 30 μg of protein are examined by polyacrylamide gel electrophoresis/western blot analysis. Molecular weight markers are indicated in kilodaltons. Arrows mark α2-AR protein bands.
Figure 11:
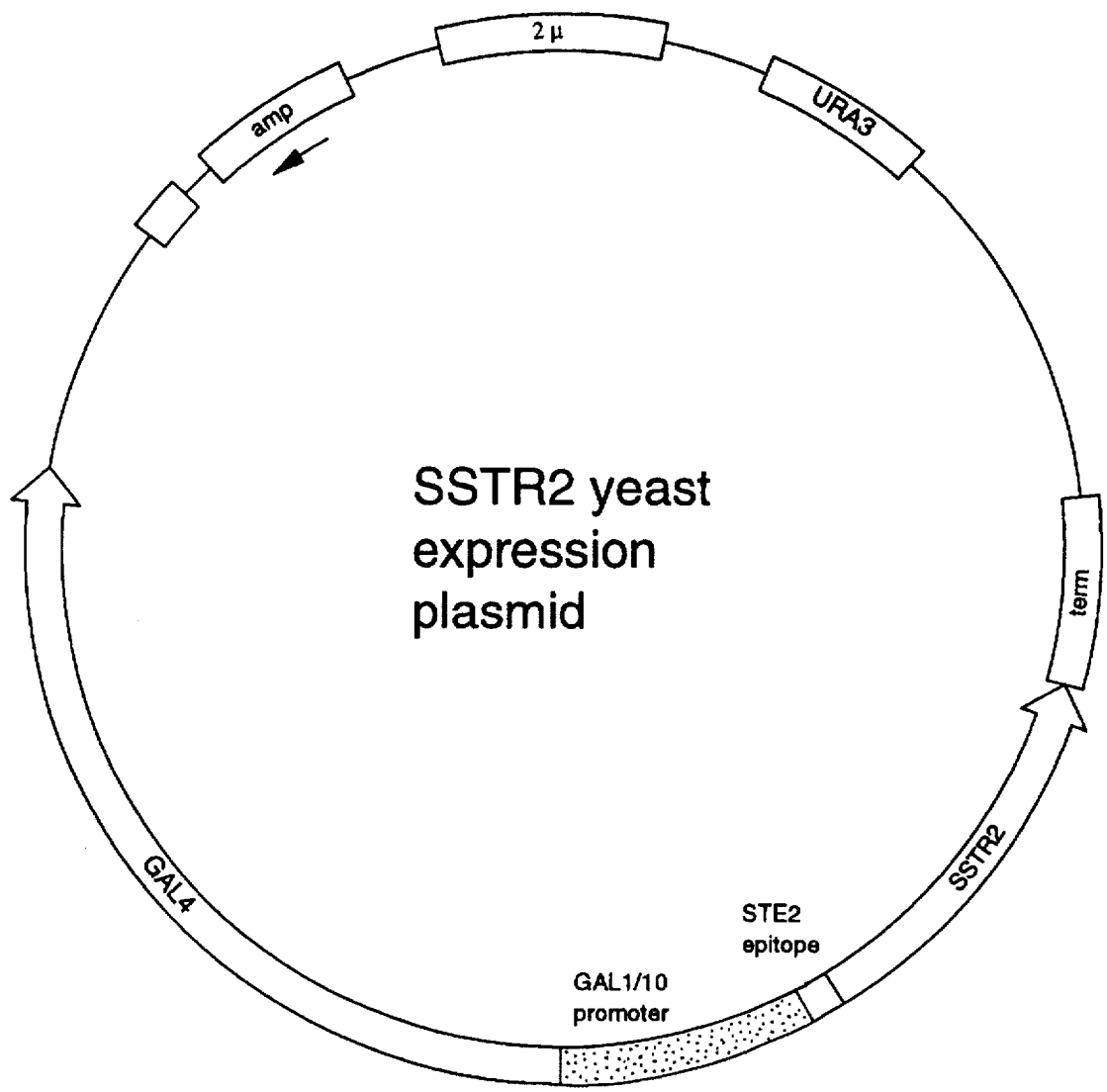
FIG. 11. Somatostatin receptor expression plasmid.

Agonist Dependent Growth of Yeast in Response to Somatotstatin Receptor Agonists Yeast strains that respond to somatostatin are created by introducing several modifications into typical laboratory yeast strains. First, a cDNA encoding the somatostatin receptor subtype 2 (SSTR2) is placed under the control of the galactose-inducible GAL1 promoter in a multicopy yeast plasmid (FIG. 10). High level expression of receptor is accomplished by inducible co-overexpression of the transcriptional activating protein GAL4 from the same plasmid. Second, the endogenous Gα protein gene, GPA1/SCG1, is replaced with a chimeric gene composed of an amino terminal domain from GPA1/SCG1, and C-terminal sequences from rat Gαi2 (FIG. 11). Expression of chimeric G proteins in yeast have previously been shown to suppress the growth defect of scg1/gpa1 mutant cells [Kang, Y. -S., Kane, J., Kurjan, J., Stadel, J. M., and Tipper, D. J. (1990) Mol. Cell. Biol. 10, 2582–2590]. Third, the FAR1 gene is deleted, permitting continued growth in the presence of an activated mating signal transduction pathway. The FAR1 protein is thought to serve as the primary interface between the mating signal transduction pathway and cell cycle machinery [Chang, F. and Herskowitz, I. (1990) Cell 63, 999–1012; Peter, M., Gartner, A., Horecka, J., Ammerer, G., and Herskowitz, I. (1993) Cell 73, 747–760; Tyers, M. and Futcher, B. (1993) Mol. Cell. Biol. 13, 5659–5669]. Fourth, the FUS1 gene is replaced with a reporter gene construct made by fusing transcription control elements of the FUS1 gene to HIS3 protein coding sequences, thereby placing expression of the HIS3 gene product under the control of the pheromone signal transduction pathway. Yeast strains (his3) bearing this construct are able to grow poorly on supplemented minimal medium lacking histidine and are sensitive to 3-amino-1,2,4-triazole (AT), an inhibitor of the HIS3 gene product. Receptor activation by agonist-binding leads to increased HIS3 protein expression, a corresponding increase in resistance to AT, and, therefore, the ability to grow on medium lacking histidine and/or in the presence of the inhibitor. Adjusting the pH of the growth medium to >pH 5.5 enhances the ability of such cells to grow in the presence of agonist, presumably due to an increased ability of somatostatin to bind to SSTR2.

Figure 13A:
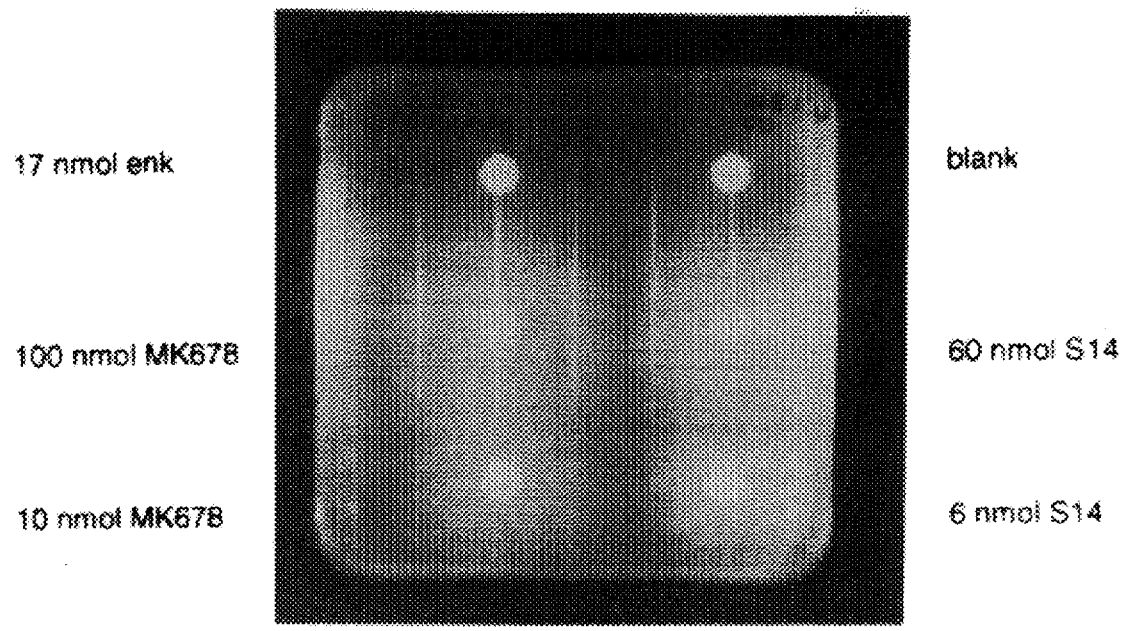
FIGS. 13A and 13B. Dose dependent growth response of yeast cells to somatostatin. Cultures of yeast strain LY268 are embedded in agar (top plate) or spread evenly on the surface of agar plates (bottom plate) and exposed to the indicated amounts of designated compounds spotted on paper disks placed on top of the agar. Plates are incubated at 30° C.
Figure 13B:
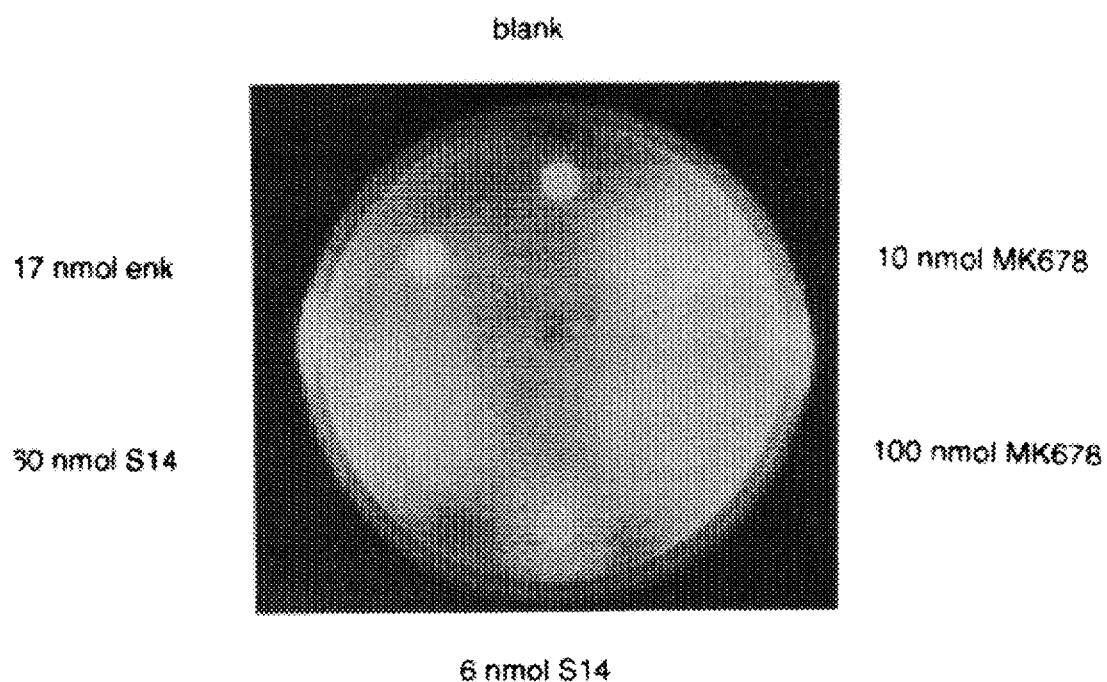

The utility of the yeast expression system lies in its adaptability to rapid mass screening. To facilitate screening for novel therapeutics directed at the SSTRs, a convenient agar plate bioassay is developed in which functional coupling of somatostatin binding to receptor and subsequent activation of the mating signal transduction pathway is detected as a zone of growth (halo) around applied compounds (FIGS. 13A and B). Overnight liquid cultures of LY268 [a derivative of YPH500 (Stratagene) MATa ura3–52 lys2-801 ade2 trp1Δ63 his3Δ200 leu2Δ1 far1ΔLYS2 scg1ΔhisG fus1ΔFUS1-HIS3 sst2ΔADE2 bearing the SSTR2 expression plasmid and the SCG1-Gαi2 expression plasmid pLP82 in SC dextrose (2%) lacking ura, trp were transferred to SC Lactate medium (2%) lacking ura and trp and subsequently SC galactose (2%) medium lacking ura and trp. Cells (2×105) are then plated in 30 ml of SC galactose (2%) lacking ura, trp, and his agar (FIG. 13A, top panel), or spread evenly on the surface (FIG. 13B, bottom panel), the indicated mounts of selected compounds applied to paper disks situated on the surface of the agar plate, and incubated at 30° C. for 3–5 days. Halos of growth are observed around disks saturated with varying concentrations of somatostatin (S-14) and MK678 [a hexapeptide analog of somatostatin that exhibits high affinity binding to SSTR2 [Veber, D., Saperstein, R., Nutt, R., Friedinger, R., Brady, P., Curley, P., Perlov, D., Paleveda, W., Zacchei, A., Cordes, E., Anderson, P., and Hirschmann, R. (1981) Life Sci. 35, 1371–1378]. Halo size increases in proportion to the amount of agonist applied and a significant response is observed even at the lowest amount applied (6 nmol S-14), demonstrating the exquisite sensitivity of the assay. No detectable response is observed with carrier alone, or to met-enkephalin, an opiate receptor agonist, demonstrating the high specificity of the assay.

Yeast medium and culture conditions are formulated according to standard procedures and DNA-mediated transformation of yeast is by the LiAc method [Sherman, F., Fink, G. R., and Hicks, J. B. (1986) Methods in Yeast Genetics (Cold Spring Harbor Laboratory Press]. LY268 is constructed by sequential insertional deletion using recombinant scg1:ΔhisG, far1::LYS2, FUS1ΔHIS3, and sst2::ADE2 alleles. The scg1::hisG allele is assembled by inserting the hisG-URA3-hisG fragment from pNKY51 [Alani, E., Cao, L., and Kleckner, N. (1987) Genetics 116, 541–545] between the 5' EcoRI-HindIII and 3' SphI-SnaBI fragments of SCG1/GPA1. After DNA-mediated transformation of appropriate yeast strains and selection for replacement of the chromosomal allele, the URA3 gene is removed by inducing recombination between hisG repeats by growth on 5-fluoroorotic acid (FOA)-containing medium [Boeke, J., Lacroute, F., and Fink, G. (1984) Mol. Gen. Genet. 197, 345–346]. The far1ΔLYS2 allele is constructed by amplifying two fragments of the FAR1 gene [Chang, F. and Herskowitz, I. (1990) Cell 63, 999–1012] from yeast genomic DNA (strain YPH501, Stratagene) using synthetic oligonucleotides that introduce an EcoRI site at position 295 and include the natural HindIII site at 1201 in the 5' fragment and an HindIII site at position 2017 and a SalI site at 2821 in the 3' fragment. The fragments are cloned into the EcoRI/SalI fragment of pBSK (Stratagene). The completed far1ΔLYS2 construct is digested with EcoRI and used to transform yeast. An EcoRI fragment encoding the FUS1-HIS3 reporter gene is released from pSL1497 [Stevenson, B. J., Rhodes, N., Errede, B., and Sprague, G. F. (1992) Genes Dev. 6, 1293] and used to transform appropriate yeast strains. The sst2ΔADE2 allele [Dietzel, C. and Kurjan, J. (1987) Mol. Cell. Biol. 7, 4169–4177] is built from a 2.5 kb fragment of the ADE2 gene amplified by PCR using oligos that placed a Cla I site at position 1 and an NheI site at position 2518. This fragment is used to replace the internal ClaI-NheI fragment in SST2. The sst2ΔADE2 fragment is released by digestion with SalI and used to transform appropriate yeast strains.

The multistep construction of the SSTR2 expression plasmid is initiated by inserting an SphI/NarI fragment of 3' untranslated region from the STE7 gene [Teague, M. A., Chaleff, D. T., and Errede, B. (1986) Proc. Natl. Acad. Sci. USA 83, 7371–7375], and an EcoRI/BamHI fragment of the GAL1/10 promoter [Yocum, R. R., Hanley, S., West, R., and Ptashne, M. (1984) Mol. Cell. Biol. 4, 1985–1998] into appropriate sites in YEp352 [Hill, J. E., Myers, A. M., Koerner, T. J., and Tzagoloff, (1986) Yeast 2, 163–167.], creating pEK1. A PCR product, encoding the open reading frame and transcriptional termination sequences of the GAL4 gene, is amplified with oligos containing 5' EcoRI and 3' AatII sites and inserted into pEK1, creating pMP3. The cDNA encoding rat SSTR2 [Strnad, J., Eppler, C. M., Corbett, M., and Hadcock, J. R. (1993) BBRC 191, 968–976] is modified by PCR using oligonucleotides that add a BglII site in the DNA sequences encoding the amino terminus of SSTR2 and a BglII site directly after the translational stop site. SSTR2 coding sequences are inserted as a BglII PCR fragment into the BamHI site of pMP3.

Figure 12:
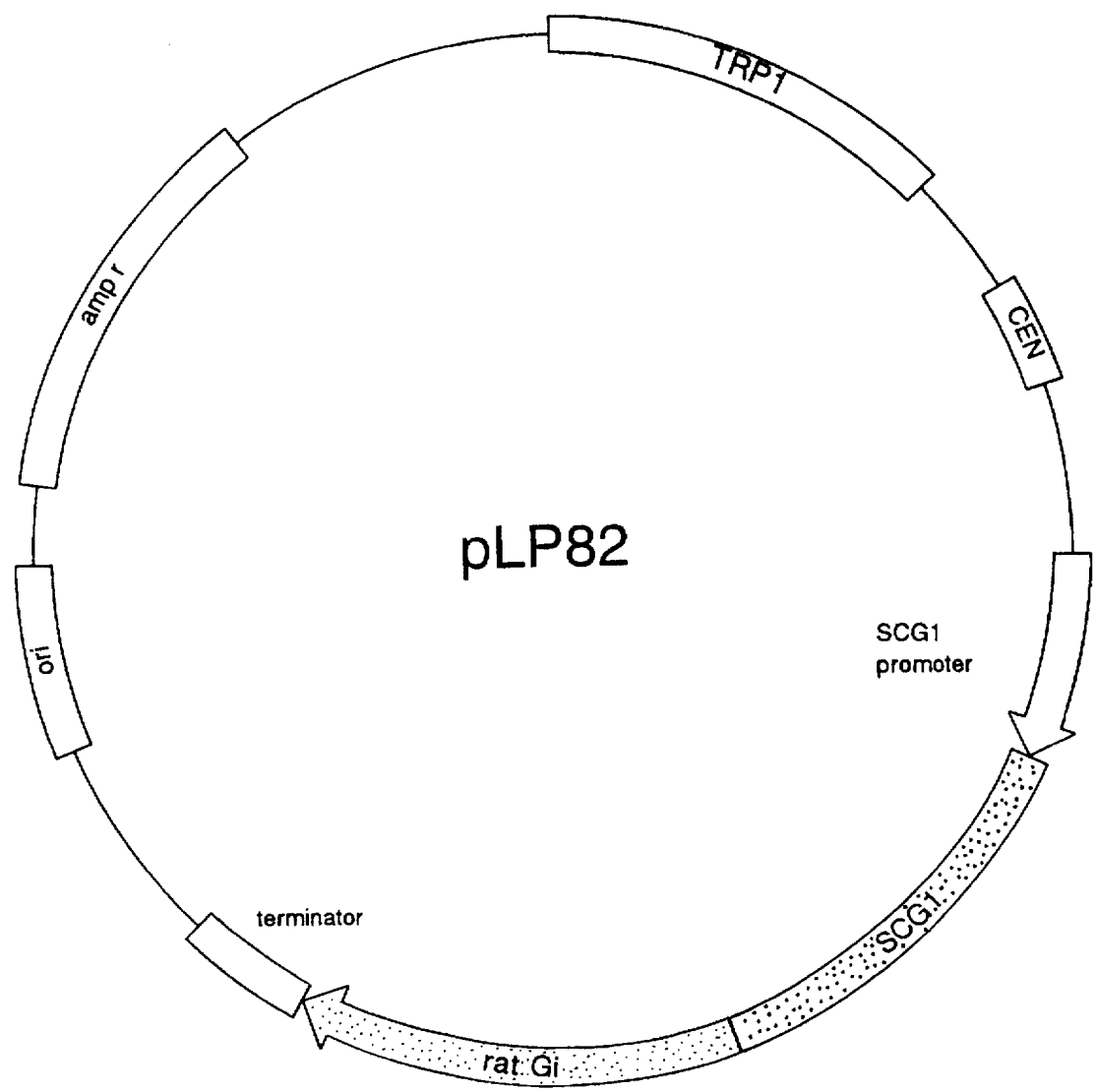
FIG. 12. G protein expression plasmid, pLP82.

Plasmid pLP82 (FIG. 12) is constructed by first replacing the XhoI/EcoRI promoter fragment in pPGKH-SCG1-Gαs [Kang, Y. -S., Kane, J., Kurjan, J., Stadel, J. M., and Tipper, D. J. (1990) Mol. Cell. Biol. 10, 2582–2590], with a modified SCG1 promoter fragment [Dietzel, C. and Kurjan, J. (1987) Cell 50, 1001–1010] amplified from yeast genomic DNA using oligonucleotides that introduce 5' XhoI and 3' EcoRI sites at positions −200 and −42, forming plasmid pLP61. The BamHI fragment encoding Gαs domain is replaced with a comparable fragment encoding Gαi2, forming plasmid pLP71. The XhoI/SalI fragment of pLP71 encoding an SCG1-Gαi2 chimeric G protein expressed under the control of the SCG1 promoter is transferred to the SalI site in pRS414 (Stratagene), forming pLP82.

Plasmid pLP83 is constructed by replacing the EcoRI fragment in pLP71 with the EcoRI fragment encoding SCG1 from pPGKH-SCG1 [Kang, Y. -S., Kane, J., Kurjan, J., Stadel, J. M., and Tipper, D. J. (1990) Mol. Cell. Biol. 10, 2582–2590], forming plasmid pLP75. The XhoI/SalI fragment encoding SCG1 is transferred to the SalI site in pRS414 (Stratagene), forming plasmid pLP83.

EXAMPLE 4

Effects of G Protein Expression on the Sensitivity of the Bioassay

Yeast strains LY268 (pLP82: CEN pSCG1-Scg1-Gαi2), LY262 (pRS414-PGK-Scg1-Gαi2:pRS414 containing the PGK-Scg1-Gαi2 Xho/SalI fragment from pPGKH-Scg1-Gαi2 in the SalI site), LY324 (pLP84: 2μ pSCG1-Scg-Gαi2), and LY284 (pRS424-PGK-Scg-Gαi2:pRS424 containing the PGK-Scg1-Gαi2 Xho/SalI fragment from pPGKH-Scg1-Gαi2 in the SalI site) were constructed by placing the designated plasmids in strain LY260 [a derivative of YPH500 (Stratagene) MATa ura 3–52 lys2–801 ade2 trp1D63 his3Δ200 leu2α1 far1ΔLYS2 scg1ΔhisG fus1ΔFUS1-HIS3 sst2ΔADE2 bearing the SSTR2 expression plasmid]. Overnight liquid cultures in SC-Dextrose (2%) lacking ura and trp were transferred to SC-Lactate (2%) medium lacking ura and trp and subsequently SC-Galactose (2%) medium lacking ura and trp. Cells ($2\times10^5$) are then plated in 30 ml of SC-Galactose (2%) lacking ura, trp, and his agar, the indicated amounts of selected compounds applied to paper disks situated on the surface of the agar plate, and incubated at 30° C. for 3–5 days (FIGS. 14A, B, C, and D). The extent of growth around S-14 is dependent upon the G protein expression plasmid contained in each strain. The most luxurient growth is observed in response to S-14 by LY268 (pLP82: CEN pSCG1-Scg1-Gαi2), less growth is seen in strains LY262 (pRS414-PGK-Scg1-Gαi2) and LY324 (pLP8 4: 2pSCG1-Scg-Gαi2), while little detectable growth is exhibited by LY284 (pRS424-PGK-Scg1-Gαi2). These results are consistent with the observed inhibition of pheromone stimulated transcriptional induction by elevated amounts of expressed Gα protein. Thus, precise regulation of G protein expression levels in strains expressing heterologous G protein-coupled receptors is critical to the design and successful implementation of a bioassay for compounds that interact with the receptor.

Plasmid pLP84 is constructed by first replacing the XhoI/EcoRI promoter fragment in pPGKH-SCG1-Gas [Kang, Y. -S., Kane, J., Kurjan, J., Stadel, J. M., and Tipper, D. J. (1990) Mol. Cell. Biol. 10, 2582–2590], with a modified SCG1 promoter fragment [Dietzel, C. and Kurjan, J. (1987) Cell 50, 1001–1010] amplified from yeast genomic DNA using oligonucleotides that introduce 5' XhoI and 3' EcoRI sites at positions –200 and –42, forming plasmid pLP61. The BamHI fragment encoding Gas domain is replaced with a comparable fragment encoding Gαi2, forming plasmid pLP71. The XhoI/SalI fragment of pLP71 encoding an SCG1-Gαi2 chimeric G protein expressed under the control of the SCG1 promoter is transferred to the SalI site in pRS424 (Stratagene), forming pLP84.

EXAMPLE 5
Somatostatin Receptor is Capable of Transmitting a Signal Through the Endogenous Yeast Gα Protein SSTR2 is thought to couple to Gαi3 in mammalian cells [Eppler, C. M., Zysk, J. R., Corbett, M., and Shieh, H. M. (1992) J. Biol. Chem. 267, 15603–15612]. However, when expressed in appropriate yeast strains (described below), SSTR2 is shown to be capable of transmitting a signal through the endogenous yeast Gα protein. Implicit in this observation is the necessary coupling of SSTR2 to the endogenous Gα protein. The ability of heterologous G protein-coupled receptors to couple to the endogenous Gα protein is a significant improvement in existing technology, and is thought not to be possible in the prior art (King K. Dohlman, H. G., Thorner, J., Caron, M. G., and Lefkowitz, R. J. (1990) Science 250, 121–123). Yeast strains LY266 (pLP83: CEN pSCG1-Scg1), LY280 (pRS414-PGK-Scg1: pRS414 containing the PGK-Scg1 Xho-SalI fragment from pPGKH-ScgI in the SalI site), LY326 (pLP86: 2μ pSCG1-Scg), and LY282 (pRS424-pPGK-Scg pRS424 containing the PGK-Scg1 Xho-SalI fragment from pPGKH-Scg1 in the SalI site) were constructed by placing the designated plasmids in strain LY260. Overnight liquid cultures of these strains, which are capable of expressing only SCG1/GPA1, in SC-Dextrose (2%) lacking ura and trp were transferred to SC-Lactate (2%) lacking ura, trp, and subsequently to SC-Galactose (2%) lacking ura and trp medium. Cells ($2\times105$) are then plated in 30 ml SC-Galactose (2%) lacking ura, trp, and his medium, the indicated amounts of selected compounds applied to paper disks situated on the surface of the agar plate, and incubated at 30° C. for 3–5 days. Halos of growth are observed around disks saturated with varying concentrations of S-14, demonstrating that a productive signal can be transduced through an interaction between SSTR2 and the yeast SCG1/GPA1 protein (FIGS. 15A, B, C, and D). These observations demonstrate that a simple and broadly applicable bioassay may be established in which any member of the class of G protein-coupled receptors may be expressed in appropriately modified yeast strains and made to couple to the endogenous Gα protein.

Plasmid pLP86 is constructed by replacing the EcoRI fragment in pLP71 with the EcoRI fragment encoding SCG1 from pPGKH-SCG1 [Kang, Y. -S., Kane, J., Kurjan, J., Stadel, J. M., and Tipper, D. J. (1990) Mol. Cell. Biol. 10, 2582–2590], forming plasmid pLP75. The XhoI/SalI fragment encoding SCG1 is transferred to the SalI site in pRS424 (Stratagene), forming plasmid pLP86.

Figure 16A:
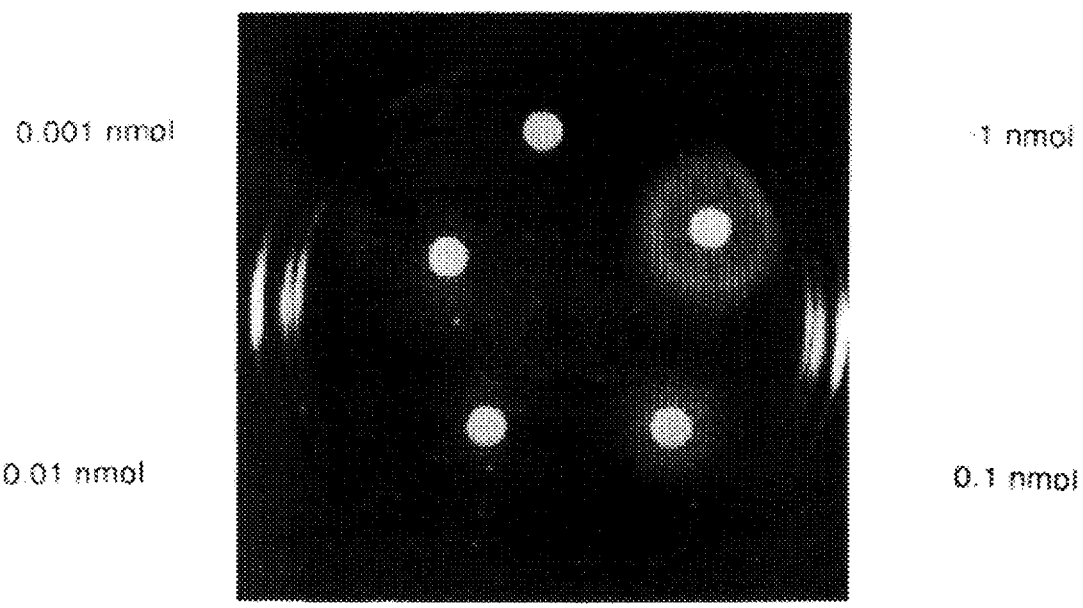
FIGS. 16A and B. Yeast cells bearing a mutation in the sst2 gene exhibit elevated resistance to AT when exposed to mating pheromone. Cultures of yeast strains are embedded in agar and exposed to the indicated amounts of designated compounds spotted on paper disks placed on top of the agar. Plates are incubated at 30° C.
Figure 16B:
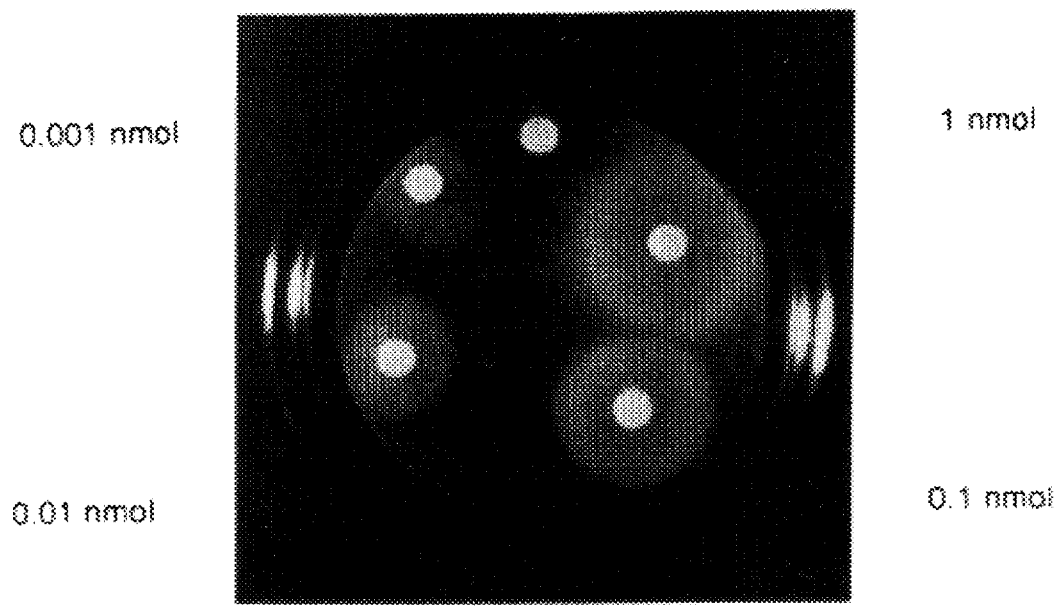

EXAMPLE 6
Mutations in SST2 Enhance the Sensitivity of the Response to Somatostatin Mutations in the SST2 gene result in supersensitivity of otherwise wild type cells to mating pheromone. The effect of this mutation on levels of AT resistance expressed in far1, FUS1-HIS3 strains is examined (FIGS. 16A and B). Cells ($2\times10^5$) from overnight cultures of LY230 [a derivative of YPH500 (Stratagene) MATa SST2 ura3–52 lys2–801 ade2 trp1Δ63 his3Δ200 leu2Δ1 far1ΔLYS2 fus1ΔFUS1-HIS3] and LY238 (a modification of LY230 sst2ΔADE2) in SCD-ura, trp are plated on SCD-ura, trp, his, containing 10 μM AT and incubated at 30° C. for 2 days. Increased AT resistance in response to mating factor is exhibited by LY238 (sst2). Growth of LY238 is observed around disks containing 10 pmol of mating pheromone, while LY230 (SST2) required 1 nmol of mating factor for significant growth to be observed. Thus, introduction of sst2 into these strains raises the sensitivity of the bioassay by at least 100-fold, opening the possibility of increasing the sensitivity of the SSTR-dependent bioassay as well.

Figures 17A, 17B, 17C, 17D:
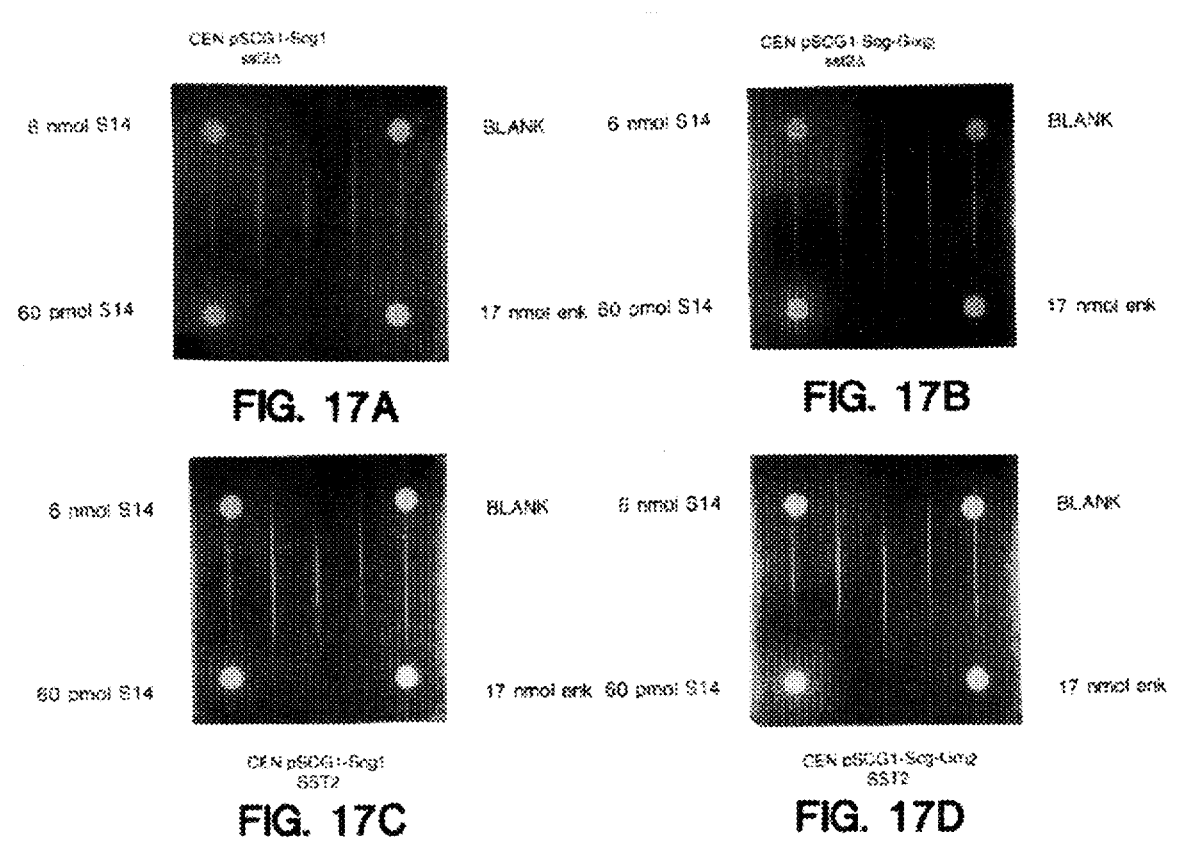

Yeast strains that express SSTR2 and bearing a defective sst2 gene exhibit much greater growth around disks containing various concentrations of somatostatin than is exhibited by strains containing a functional SST2 gene. Overnight cultures of strains LY268 (sst2, containing pLP82), LY266 (sst2, containing pLP83), LY288 [a derivative of YPH500 (Stratagene) MATa SST2 ura3–52 lys2–801 ade2 trp1Δ63 his3Δ200 leu2Δ1 far1ΔLYS2 scg1ΔhisG fus1ΔFUS1-HIS3 bearing the SSTR2 expression plasmid and the SCG1-Gαi2 expression plasmid, pLP82] and LY290 (a modification of LY288 that contains LP83) in SC Dextrose (2%) lacking ura, trp were transferred to SC Lactate medium (2%) lacking ura and trp, and subsequently to SC Galactose (2%) medium lacking ura and trp. Cells ($2\times10^5$) are then plated in 30 ml SC Galactose (2%) plates lacking ura, trp, and his, the indicated amounts of selected compounds applied to paper disks situated on the surface of the agar plate, and incubated at 30° C. for 3–5 days. Halos of growth are observed around disks saturated with varying concentrations of S-14 in both sst2A and SST2 strains (FIGS. 17A, B, C, and D), however, the amount of growth exhibited by strain LY268 and LY266 (sst2) is significantly greater than that observed for strains LY288 and LY290 (SST2). Furthermore, the down-regulatory effect SST2 is more pronounced in those strains that express solely the wild type SCG1/GPA1 protein, consistent with the expectation that SST2 interacts more faithfully with the native protein than the SCG1-Gαi2 chimeric protein. Thus, introduction of mutations that interfere with sst2 function into strains expressing heterologous G protein-coupled receptors constitutes a significant improvement on wild type strains and enables the development of extremely sensitive bioassays for compounds that interact with the receptors. Other mutations e.g. STE50, sgv1, ste2, ste3, pik1, and afr1, have the similiar effect of increasing the sensitivity of the bioassay.

What is claimed is:

1. A transformed yeast cell comprising a reporter gene under control of a pheromone-responsive promoter, a heterologous protein-coupled receptor gene, each said gene being under the control of a separate promoter, and a gene mutation causing increased sensitivity to receptor activation selected from the group consisting of: sst2, STE50, sgv1, ste2, ste3, pik1, and afr1.

2. The yeast cell of claim 1 further comprising a mutation at a gene that permits transcriptional activation of pheromone-responsive genes without cell cycle arrest.

3. A transformed yeast cell comprising a reporter gene under control of a pheromone-responsive promoter, a heterologous G protein-coupled receptor gene, each said gene being under the control of a separate promoter, and a mutation at a FAR1 or FUS3 gene that permits transcriptional activation of pheromone-responsive genes without cell cycle arrest.

4. The yeast cell of claim 3 further comprising a mutation of the cdc35 gene.

5. The yeast cell of claim 4 further comprising a heterologous adenylylcyclase.

6. The yeast cell of claim 3 further comprising a mutation in the pic1 gene.

7. The yeast cell of claim 6 further comprising a heterologous PLC-β.

8. The transformed yeast cell of claim 3 further comprising a heterologous G protein-gated potassium channel wherein said yeast cell is unable to grow on low potassium media.

9. The yeast cell of claim 8 further comprising trk1 and trk2 mutations.

10. The yeast cell of claim 8 further comprising heterologous Gβγ subunits.

11. The yeast cell of claims 3, 4, 6, or 7, wherein the reporter gene is selected from the group consisting of HIS3, G418r, URA3, LYS2, CAN1, and Lacz, and the pheromone-responsive promoter is FUS1.

12. The yeast cell of claim 11 further comprising a gene mutation causing increased sensitivity to receptor activation selected from the group consisting of sst2, STE50, sgv1, ste2, ste3, pik1, and afr1.

13. The yeast cell of claim 11 further comprising a mutation in a SCG1/GPA1 gene.

14. The yeast cell of claim 13 further comprising a gene mutation causing increased sensitivity to receptor activation selected from the group consisting of sst2, STE50, sgv1, ste2, ste3, pik1, and afr1.

15. A transformed yeast cell comprising a reporter gene under control of a pheromone-responsive promoter, a heterologous G protein-coupled receptor gene, each said gene being under the control of a separate promoter, a mutation in a SCG1/GPA1 gene, and a hybrid Gα protein.

16. The hybrid Gα protein of claim 15 comprising yeast Gα protein sequences and heterologous Gα protein sequences.

17. The yeast cell of claim 15 further comprising a gene mutation causing increased sensitivity to receptor activation selected from the group consisting of sst2, STE50, sgv1, ste2, ste3, pik1, and afr1.

18. The yeast cell of claim 17 further comprising a mutation at a gene that permits transcriptional activation of pheromone-responsive genes without cell cycle arrest.

19. The yeast cell of claims 1 and 15, wherein the reporter gene is selected from the group consisting of HIS3, G418r, URA3, LYS2, CAN1, and Lacz, and the pheromone-responsive promoter is FUS1.

20. The yeast cell of claim 19 further comprising a mutation at a FAR1 or FUS3 gene that permits transcriptional activation of pheromone-responsive genes without cell cycle arrest.

21. The yeast cell of claim 19 further comprising a mutation at a gene that permits transcriptional activation of pheromone-responsive genes without cell cycle arrest.

22. The yeast cell of claims 1, 2, 3, 4, 6, 8, or 15 further comprising a heterologous Gα subunit including, but not limited to, Gs subunits, Gi subunits, Go subunits, Gz subunits, Gq subunits, G11, subunits, G16 subunits.

23. The heterologous G protein-coupled receptor gene of claims 1, 2, 3, 4, 6, 8 or 15 encodes a receptor selected from the group consisting of β2 adrenergic receptor, α2-adrenergic receptor, 5HT-1A receptor, muscarinic acetylcholine receptor, growth hormone releasing factor receptor, and somatostatin receptor.

24. A transformed yeast cell having a mutation in a SCG1/GPA1 gene comprising a reporter gene under the control of a pheromone-responsive promoter, and a DNA expression vector capable of expressing a hybrid receptor, said receptor being capable of binding to yeast G protein.

25. The transformed yeast cell of claim 24 wherein said hybrid receptor comprises sequences from yeast receptors, including intracellular sequences, and sequences from heterologous receptors.

26. The transformed yeast cell of claim 25 wherein the sequences from the yeast receptors are selected from the group consisting of STE2 or STE3.

27. The yeast cell of claim 24, wherein the reporter gene is selected from the group consisting of HIS3, G418r, URA3, LYS2, CAN1, and Lacz, and the pheromone-responsive promoter is FUS1.

28. The yeast cell of claim 27 further comprising a mutation at a gene that permits transcriptional activation of pheromone-responsive genes without cell cycle arrest.

29. The yeast cell of claim 27 further comprising a gene mutation causing increased sensitivity to receptor activation selected from the group consisting of sst2, STE50, sgv1, ste2, ste3, pik1, and afr1.

30. The yeast cell of claim 29 further comprising a mutation at a gene that permits transcriptional activation of pheromone-responsive genes without cell cycle arrest.

31. The yeast cell of claim 24 further comprising a mutation at a gene that permits transcriptional activation of pheromone-responsive genes without cell cycle arrest.

* * * * *

Adverse Decisions in Interference

Patent No. 5,691,188, Mark H. Pausch, Bradley A. Ozenberger, John R. Hadcock, Laura A. Price, Eileen M. Kajkowski, Donald R. Kirsch, and Deborah T. Chaleff, TRANSFORMED YEAST CELLS EXPRESSING HETEROLOGOUS G-PROTEIN COUPLED RECEPTOR, Interference No. 105,462, final judgment adverse to the patentees rendered May 3, 2007, as to claims 15, 16, 19, 22, and 23.

*(Official Gazette September 25, 2007)*